United States Patent
Dione et al.

(10) Patent No.: US 7,025,725 B2
(45) Date of Patent: *Apr. 11, 2006

(54) THREE-DIMENSIONAL ULTRASOUND COMPUTED TOMOGRAPHY IMAGING SYSTEM

(75) Inventors: Donald P. Dione, Deep River, CT (US); Lawrence H. Staib, Orange, CT (US); Wayne Smith, London (CA)

(73) Assignee: Ultrasound Detection Systems, LLC, Madison, CT (US)

(*) Notice: Subject to any disclaimer, the term of this patent is extended or adjusted under 35 U.S.C. 154(b) by 0 days.

This patent is subject to a terminal disclaimer.

(21) Appl. No.: 10/940,299

(22) Filed: Sep. 13, 2004

(65) Prior Publication Data

US 2005/0054924 A1 Mar. 10, 2005

Related U.S. Application Data

(63) Continuation of application No. 10/402,588, filed on Mar. 28, 2003, now Pat. No. 6,878,115.

(60) Provisional application No. 60/368,453, filed on Mar. 28, 2002.

(51) Int. Cl.
*A61B 8/00* (2006.01)

(52) U.S. Cl. ...................... 600/443; 128/916

(58) Field of Classification Search ........ 600/437–472; 73/625, 626; 128/916
See application file for complete search history.

(56) References Cited

U.S. PATENT DOCUMENTS

| | | | |
|---|---|---|---|
| 4,105,018 A | 8/1978 | Greenleaf et al. | 128/2 |
| 4,279,157 A | 7/1981 | Schomberg et al. | 73/618 |
| 4,317,369 A | 3/1982 | Johnson | 73/607 |
| 4,328,707 A | 5/1982 | Clement et al. | 73/618 |
| 4,478,084 A | 10/1984 | Hassler et al. | 73/620 |
| 4,509,368 A | 4/1985 | Whiting et al. | 73/624 |
| 4,541,436 A | 9/1985 | Hassler et al. | 128/660 |
| 5,179,455 A | 1/1993 | Garlick | 359/9 |
| 5,212,571 A | 5/1993 | Garlick et al. | 359/9 |
| 5,329,817 A | 7/1994 | Garlick et al. | 73/605 |
| 5,546,945 A | 8/1996 | Soldner | 128/661.02 |
| 5,588,032 A | 12/1996 | Johnson et al. | 378/8 |
| 5,627,906 A | 5/1997 | Walach | 382/128 |
| 5,673,697 A | 10/1997 | Bryan et al. | 128/660.07 |

(Continued)

OTHER PUBLICATIONS

Robinson, B. et al. The Scattering of Ultrasound by Cylinders: Implications for Diffraction Tomography, *J. Acoust. Soc. Am.* 80 (1), Jul. 1986 p. 40-49.

(Continued)

*Primary Examiner*—Ali Imam
(74) *Attorney, Agent, or Firm*—Wiggin and Dana LLP; Gregory S. Rosenblatt; Elizabeth A. Galletta

(57) ABSTRACT

A three-dimensional (3-D) ultrasound computed tomography (UCT) system for providing a 3-D image of a target is presented. The 3-D UCT system includes an imaging chamber having a plurality of piezoelectric elements. The plurality of piezoelectric elements are arranged as a plurality of cylindrical rings. When activated, the plurality of piezoelectric elements generate and receive an ultrasound signal in a cone beam form. The 3-D UCT system also includes a processor coupled to the imaging chamber. The processor receives and processes the ultrasound signal and constructs the 3-D image of the target. A display device is also included with the 3-D UCT system. The display device exhibits the 3-D image of the target for analysis.

23 Claims, 8 Drawing Sheets

U.S. PATENT DOCUMENTS 6,005,916 A     12/1999    Johnson et al. ............. 378/87
2003/0220569 A1*  11/2003  Dione et al. ............. 600/443

OTHER PUBLICATIONS

Sethian, J. et al. Ordered upwind methods for static Hamilton-Jacobi equations, *Applied Mathematics* (2001).

Rotten, D., et al. Analysis of normal breast tissue and of solid breast masses using three-dimensional ultrasound mammography, *Ultrasound Obstet. Gynecol.* 1999; 14: 114-124.

Bassett, L. et al. Automated and Hand-held Breast US: Effect on Patient Management, *Radiology* 1987; 165: 103-108.

Carson, P. et al. Breast Imaging in Coronal Planes with Simultaneous Pulse Echo and Transmission Ultrasound, *Science*, vol. 214,p. 1141-1143, 1981.

www.imaginis.net/breasthealth/statistics.asp (*no longer available*).

Feig, S.A., Role and Evaluation of Mammography and Other Imaging Methods for Breast Cancer Detection, Diagnosis, and Staging. *Seminars in Nuclear Medicine*, (1999) 29(1); pp. 3-15.

Christoyianni, I. ,et al., Fast Detection of Masses in Computer-Aided Mammography. *IEEE Signal Processing Magazine*, (2000) pp. 54-64.

Drukker, B.H., Breast Disease: A Primer on Diagnosis and Management. *Int. J. Fertil.*, 1997, 42 (5) p. 278-287.

http://www.nlm.nih.gov/medlineplus/news/fullstory. 597. html (*no longer available*).

Moss, H.A., et al., How Reliable is Modern Breast Imaging in Differentiating Benign from Malignant Breast Lesions in the Symptomatic Population? *Clinical Radiology*, 1999 54: p. 676-682.

Teh, W., et al. The Role of Ultrasound in Breast Cancer Screening. A Consensus Statement by the European Group for Breast Cancer Screening, *European Journal of Cancer*, 1998 34(4): p. 449-45.

Greenleaf, J.F., et al. Algebraic Reconstruction of Spatial Distributions of Acoustic Absorption Within Tissue from Their Two-Dimensional Acoustic Projections, *Acoustical Holography*, 1974 5: p. 591-603.

http://www.imaginis.net/breasthealth/biopsy/ (*no longer available*).

http://www.tricaresw.af.mil/breasted/hospital/read_the_book/toc.htm (*No longer available*).

Greenleaf, J.F., et al., Clinical Imaging with Transmissive Ultrasonic Computerized Tomography, *IEEE Transactions of Biomedical Engineering*, 1981 BME-28(2): p. 177-185.

Glover, G.H., Computerized Time-of-Flight Ultrasonic Tomography for Breast Examination, *Ultrasound Med. Biol.*, 1977 3: p. 117-127.

Scherzinger, A.L., et al., Assessment of Ultrasonic Computed Tomography in Symptomatic Breast Patients by Discriminant Analysis, *Ultrasound in Med. and Biol.* 1989 15 (1): p. 21-28.

Samuels, T.H., Breast Imaging: A Look at Current and Future Technologies, *Postgraduate Medicine*, 1998 104(5): p. 91-101.

Newman, J. Recent Advances in Breast Cancer Imaging, *Radiologic Technology*, 1999 71(1): p. 35-54.

Lehman, C.D., et al., Evaluation of Real-Time Acoustical Holography for Breast Imaging and Biopsy Guidance, *SPIE*, 1999 3659: p. 236-243.

Azhari, H. et al., Hybrid Ultrasonic Computed Tomography, *Computers and Biomedical Research*, 1997 30: p. 35-48.

Andre, M.P., et al., High-Speed Data Acquisition in a Diffraction Tomography System Employing Large-Scale Toroidal Arrays, *International Journal of Imaging Systems Technology*, 1997 8(1): p. 137-147.

Andre, M.P. et al., A New Consideration of Diffraction Computed Tomography for Breast Imaging: Studies in Phantoms and Patients, *Acoustical Imaging J.P. Jones, Ed.* 1995 p. 379-390.

Schreiman, J.S. et al., Ultrasound Transmission Computed Tomography of the Breast, *Radiology*, 1984. 150: p. 523-530.

Glover, G.H. et al., Reconstruction of Ultrasound Propogation Speed Distributions in Soft Tissue: Time-of-Flight Tomography, *IEEE Transactions on Sonics and Ultrasonics*, 1977 SU-24(4): p. 229-234.

Jones, H.W., Recent Activity in Ultrasonic Tomography, *Ultrasonics*, 1993 31(5):p. 353-360.

Greenleaf, J.F. et al., Signal Processing Methods for Transmission Ultrasonic Computerized Tomography, *Ultrasonics Symposium Proceedings*, 1980, p. 966-972.

Jago, J.R. et a.l, Experimental Studies in Transmission Ultrasound Computed Tomgraphy, *Phys. Med. Biol.*, 1991 36(11):p. 1515-1527.

Meyer, C.R. et al, A Method for Reducing Multipath Artifacts in Ultrasonic Computed Tomography, *J. Acoust. Soc. Am.*, 1982 72 (3): p. 820-823.

Pan, K.M. et al., Tomographic Reconstruction of Ultrasonic Attentuation with Correction for Refractive Errors, *IBM J. Res. Develop.*, 1981 25(1):p. 71-82.

Chenevert, T.L et al., Ultrasonic Computed Tomography of the Breast, *Radiology* 1984 152: p. 155-159.

Schmitt, R.M., et al., Error Reduction in Through Transmission Tomography Using Large Receiving Arrays with Phase-Insensitive Signal Processing, *IEEE Transaction on Sonics and Ultrasonics*, 1984 SU-31 (4): p. 251-258.

Klepper, J.R., et al., Application of Phase-Insensitive Detection and Frequency-Dependent Measurements to Computed Ultrasonic Attenuation Tomography, *IEEE Transaction on Biomedical Engineering*, 1981 BME-28(2): p. 186-201.

Andersen, A.H. et al., Digital Ray Tracing in Two-Dimensional Refractive Fields, *J. Acoust. Soc. Am.*, 1982, 72 (5): p. 1593-1606.

Andersen, A.H., A Ray Tracing Approach to Restoration and Resolution Enhancement in Experimental Ultrasound Tomography, *Ultrasound Imaging*, 1990, 12: p. 268-291.

Andersen, A.H., et al., Ray Linking for Computed Tomography by Rebinning of Projection Data, *J. Acoust. Soc. Am.*, 1987, 81 (4): p. 1990-1192.

Norton, S.J,. Computing Ray Trajectories Between Two Points: A Solution to the Ray-Linking Problem, *Optical Society of America*, 1987 4(10): p. 1919-1922.

Mueller, R.K. et al., Reconstruction Tomography and Applications to Ultrasonics, *Proceedings of the IEEE*, 1979 67(4): p. 567-587.

Ladas, K.T., et al,. Application of an ART in an Experimental Study of Ultrasonic Diffraction Tomography, *Ultrasonic Imaging*, 1993, 15: p. 48-58.

Sponheim, N. et al., Experimental Results in Ultrasonic Tomography Using a Filtered Backpropagation Algorithm, *Ultrasonic Imaging*, 1991 13:p. 56-70.

Pan, X., Unified Reconstruction Theory for Diffraction Tomography, with Consideration of Noise Control, *J.Opt. Soc. Am.A.*, 1998, 15: p. 2312-2326.

Manry, C.W.J. et al., The FDTD Method for Ultrasound Pulse Propagation Through a Two-Dimensional Model of the Human Breast, *J. Acoust. Soc. Am.*, 1993, 94(3): p. 1774-1775.

Lu, C. et al., Image Reconstruction with Acoustic Measurement Using Distorted Born Iteration Method, *Ultrasonic Imaging*, 1996, 18:p. 140-156.

Lu, Z-Q. et al., Acoustical Tomography Based on the Second-Order Born Transform Perturbation Approximation. *IEEE Transactions on Ultrasonics, Ferroelectrics, and Frequency Control*, 1996. 43(2):p. 296-302.

Borup, D.T., S.A. Johnson, W.W. Kim, M.J. Berggren, Nonpertubative Diffraction Tomography Via Gauss-Newton Iteration Applied to the Scattering Integral Equation. *Ultrasonic Imaging*, 1992. 14: p. 69-85.

Manry, C.W.J., S.L. Broschat, Inverse Imagining of the Breast with a Material Classification Technique. *J. Acoust. Soc. Am.*, 1998. 103(3): p. 1538-1546.

Lu, Z.-Q., C.-H. Tan, Z.-Y. Tao, Q. Xue, Acoustical Diffraction Tomography in a Finite Form and Its Computer Simulations. *IEEE Transactions on Ultrasonics, Ferroelectrics, and Frequency Control*, 2001. 48(4): p. 969-975.

Devaney, A.J., Generalized Projection-Slice Theorem for Fan Beam Diffraction Tomography. *Ultrasonic Imaging*, 1985, 7: p. 264-275.

Devaney, A.J., G. Beylkin, Diffraction Tomography Using Arbitrary Transmitter and Receiver Surfaces. *Ultrasonic Imaging*, 1984, 6: p. 181-193.

Witten, A., J. Tuggle, R.C. Waag, A Practical Approach to Ultrasonic Imaging Using Diffraction Tomography, *J. Acoust. Soc. Am.*, 1988. 83(4): p. 1645-1652.

Robinson, B.S., J.F. Greenleaf, The Scattering of Ultrasound by Cylinders: Implications for Diffraction Tomography. *Acoustical Society of America*, 1986. 80(1): p. 40-49.

Anastasio, M.A., X. Pan, Computationally Efficient and Statistically Robust Image Reconstruction in Three-Dimensional Diffraction Tomography. *J. Opt. Soc. Am. A*, 2000. 17(3): p. 391-400.

Trahey, G.E., P.D. Freiburger, L.F. Nock, D.C. Sullivan, In Vivo Measurements of Ultrasonic Beam Distortion in the Breast. *Ultrasonic Imagining*, 1991. 13: p. 71-90.

Zhu, Q., B.D. Steinberg, Wavefront Amplitude Distribution in the Female Breast. *J. Acoustical Society of America*, 1994. 96(1): p. 1-9.

Kossoff, G., E.K. Fry, J. Jellins, Average Velocity of Ultrasound in the Human Female Breast. *The Journal of the Acoustical Society of America*, 1973. 53(6): p. 1730-1736.

Yang, J.N., A.D. Murphy, E.L. Madsen, J.A. Zagzebski, K.W. Gilchrist, G.R. Frank, M.C. Mcdonald, C.A. Millard, A. Faraggi, C.A. Jaramillo, F.R. Gosset, A Method for In Vitro Mapping of Ultrasonic Speed and Density in Breast Tissue. *Ultrasonic Imaging*, 1991. 13: p. 91-109.

Arditi, M., P.D. Edmonds, J.F. Jensen, C.L. Mortensen, W.C. Ross, P. Schattner, D.N. Stephens, W. Vinzant, Apparatus for Ultrasound Tissue Characterization of Excised Specimens. *Ultrasonic Imaging*, 1991. 13: p. 280-297.

Edmonds, P.D., C.L. Mortensen, J.R. Hill, S.K. Holland, J. F. Jensen, P. Schattner, A.D. Valdes, Ultrasound Tissue Characterization of Breast Biopsy Specimens. *Ultrasonic Imaging*, 1991. 13: p. 162-185.

Landini, L., R. Sarnelli, F. Squartini, Frequency-Dependent Attenuation in Breast Tissue Characterization, *Utrasound in Med. & Biol.*, 1985. 11(4): p. 599-603.

Berger, G., P. Laugier, J.C. Thalabard, J. Perrin, Global Breast Attenuation: Control Group and Benign Breast Diseases, *Ultrasonic Imaging*, 1990. 12: p. 47-57.

Andre, M.P., H.S. Janee, M.Z. Ysrael, J. Hodler, L.K. Olson, G.R. Leopold, R. Schultz, Three-Dimensional Holographic Display of Ultrasound Computed Tomograms, *SPIE*, 1997. 3031: p. 631-642.

Greenleaf, J.F., J. Ylitalo, J.J. Gisvold, Ultrasonic Computed Tomography for Breast Examination, *IEEE Engineering in Medicine and Biology Magazine*, 1987: p. 27-32.

Zhang, D., X. Chen, X-f. Gong, Acoustic Nonlinearity Parameter Tomography for Biological Tissues Via Parametric Array from a Circular Piston Source—Theoretical Analysis and Computer Simulations, *J. Acoust. Soc. Am.*, 2001. 109(3): p. 1219-1225.

Bamber, J.C., C.R. Hill, Ultrasonic Attenuation and Propagation Speed in Mammalian Tissues as a Function of Temperature, *Ultrasound in Med. And Biol.*, 1979. 5: p. 149-157.

Lanza, G.M., K.D. Wallace, M.J. Scott, W.P. Cacheris, D.R. Abendscheim, D.H. Christy, A.M. Sharkey, J.G. Miller, P.J. Gaffney, S.A. Wickline, A Novel Site-Targeted Ultrasonic Contrast Agent With Broad Biomedical Application, *Circulation*, 1996. 94(12): p. 3334-3340.

Paganelli, G., P. Magnani, F. Zito, E. Villa, F. Sudati, L. Lopalco, C. Rossetti, M. Malcovati, F. Chiolerio, E. Seccamani, A.G. Siccardi, F. Fazio, Three-Step Monoclonal Antibody Tumor Targeting in Carcinoembryonic Antigenpositive Patients, *Cancer Research*, 1991. 51: p. 5960-5966.

http://cbshealthwatch.medscape.com/medscape/p/ G_library/article. asp?RecID=234435&ContentType=Library&NB=2&S P=2&Channel=5 (No longer available).

Greenleaf, J.F., S.A. Johnson, A.H. Lent, Measurement of Spatial Distribution of Refractive Index in Tissues by Ultrasonic Computer Assisted Tomography, *Ultrasound in Med. & Biol.*, 1978. 3: p. 327-339.

Greenleaf, J.F., S.A. Johnson, Acoustic Examination, Material Characterization and Imaging of the Internal Structure of a Body by Measurement of the Time-of-Flight of Acoustic Energy Therethrough, 1978, University of Utah: U.S.A.

Sponheim, N., L.J. Gelius, I. Johansen, J.J. Stamnes, Quantitative Results in Ultrasonic Tomography of Large Object Using Line Sources and Curved Detector Arrays, *IEEE Transactions on Ultrasonic, Ferroelectrics, and Frequency Control*, 1991. 38(4): p. 370-379.

Dione, D.P., P. Shi, W. Smith, P. DeMan, J. Soares, J. Duncan, A. Sinusas, Three-Dimensional Regional Left Ventricular Deformation from Digital Sonomicrometry. 19th *Annual International Conference of the IEEE Engineering in Medicine and Biology Society*, 1997. p. 848-851.

Meoli, D., R. Mazhari, D. Dione, J. Omens, A. McCullouch, A. Sinusas, Three-Dimensional Digital Sonomicrometry: Comparison with Biplane Radiology. Proceedings of 24th *IEEE Northeast Bioengineering Conference*, 1998.

Kak, A.C., M. Slaney, Principles of Computerized Tomographic Imaging. 1988: *IEEE Press*.

Andersen, A.H., A.C. Kak, Simultaneous Algebraic Reconstruction Technique (SART): A Superior Implementation of the Art Algorithm. *Ultrasonic Imaging*, 1984. 6: p. 81-94.

Vannier, M.W., C.F. Holdebolt, J.L. Marsh, Craniosynostosis: Diagnostic Value of Three-dimensional CT Reconstruction. *Radiology*, 1989. 173: p. 669-673.

http://noodle.med.yale.edu/~papad/research/surfaceEdit/surfaceedit.html.

Madsen, E.L., E. Kelly-Fry, F.R. Frank, Anthropomorphic Phantoms for Assessing Systems used in Ultrasound Imaging of the Compressed Breast. *Ultrasound in Med. Biol.*, 1988. 14(Sup. 1): p. 183-201.

Dempsey, P.J., Breast Sonography: Historical Perspective, Clinical Application, and Image Interpretation. *Ultrasound Quarterly*, 1988. 6(1): p. 69-90.

* cited by examiner

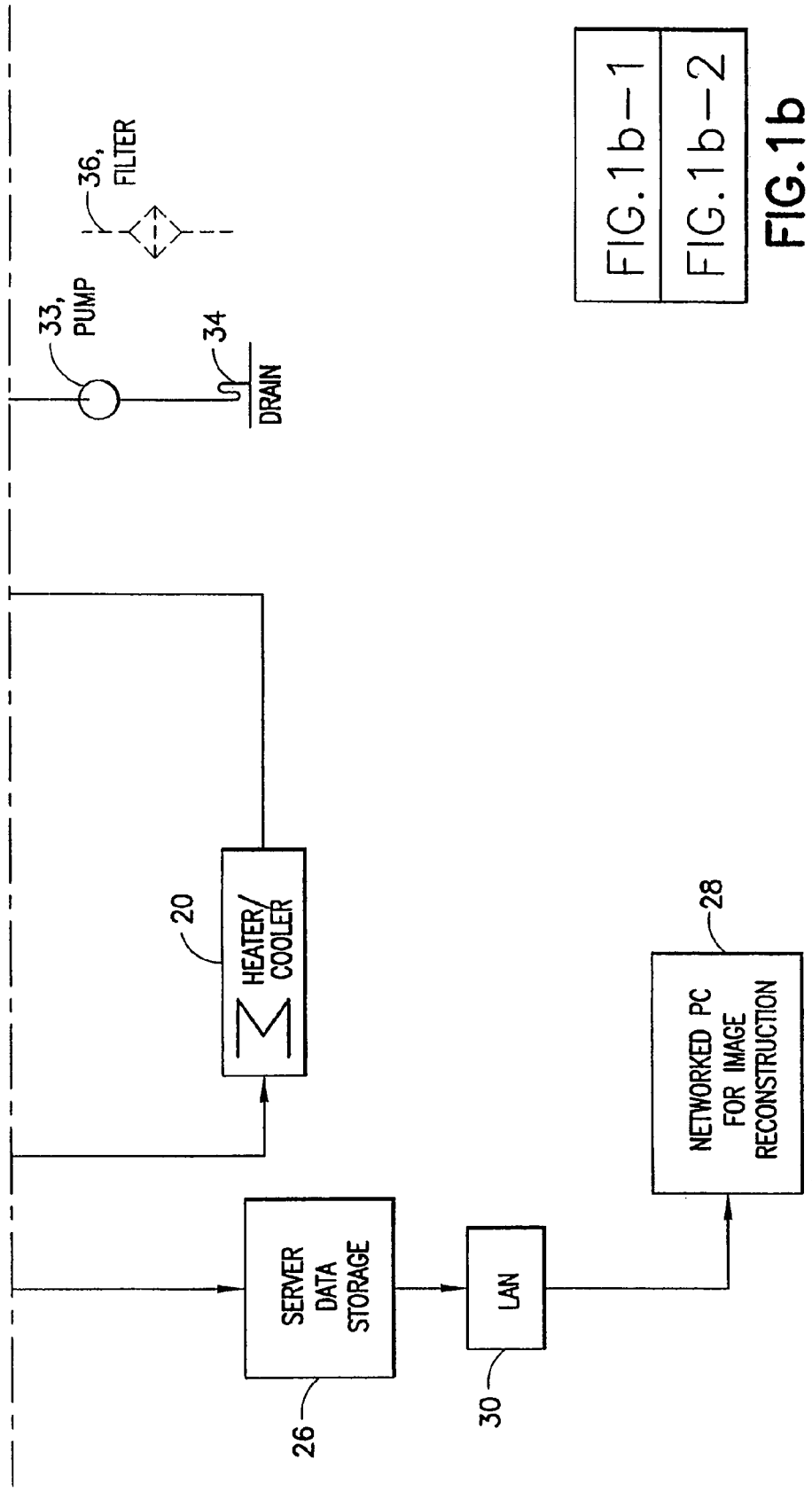

CYLINDER VOLUME FORMULA

THE VOLUME V OF ANY CYLINDER WITH RADIUS r AND HEIGHT h IS EQUAL TO THE PRODUCT OF THE AREA OF A BASE AND THE HEIGHT.

FORMULA: $V = \pi r^2 h$

US 7,025,725 B2

THREE-DIMENSIONAL ULTRASOUND COMPUTED TOMOGRAPHY IMAGING SYSTEM

CROSS REFERENCE TO RELATED APPLICATIONS

This is a continuation of application Ser. No. 10/402,588, now U.S. Pat. No. 6,878,115, filed on Mar. 28, 2003 entitled "Three-Dimensional Ultrasound Computed Tomography Imaging System," which claims priority from U.S. Provisional Patent Application Ser. No. 60/368,453, filed on Mar. 28, 2002 also entitled "Three-Dimensional Ultrasound Computed Tomography Imaging System," the disclosures of which are incorporated by reference herein in their entireties.

BACKGROUND OF THE INVENTION

This invention relates generally to a system and method for generating three-dimensional (3-D) images of objects to permit non-destructive inspection of the object in fields such as, for example, medical diagnostics.

The American Cancer Society estimates that in 2001 approximately 192,200 new cases of invasive breast cancer (Stages I–IV) can be diagnosed among women in the United States. Another 46,400 women can be diagnosed with ductal carcinoma in situ, a non-invasive breast cancer. It is has been estimated that over 40,000 deaths can occur from breast cancer in the United States annually. Early detection of breast cancer is vital since early detection has repeatedly been shown to improve the chance of survival. Currently, mammography is a preferred modality for early detection of breast cancer. However, mammography is problematic due to the use of potentially harmful ionizing radiation. Since asymptomatic women are screened repeatedly and the effects of radiation are cumulative, it is recommended that ionizing radiation be avoided. Other limitations include the following: 1) mammography is a two-dimensional (2D) projection modality and is therefore subject to superposition artifacts (i.e. features lying on or near the same line of projection can easily be obscured or made indistinct.); 2) mammography typically cannot differentiate malignant from benign lesions and therefore a subsequent test such as a biopsy is needed; and 3) mammography has a sensitivity of approximately 90% and therefore does not detect an estimated 8–22% of palpable breast cancers. Another modality, echo ultrasound imaging is commonly used as an adjunct to mammography because of its ability to discriminate a cyst from a solid mass. Studies have shown that echo ultrasound, however, has not proven to be an effective screening modality. Screening is the use of a modality to detect disease in an asymptomatic population. Echo ultrasound has a limited field of view, is not reproducible, and produces results that are a balance between depth of imaging (penetration of ultrasound) and image resolution.

Therefore, there is a need for a new, safe and accurate (sensitive and specific) modality. The system of the present invention is a novel three-dimensional (3-D) approach to ultrasound computed tomography which can provide such a modality. In 1974, Greenleaf et al. first published a technique called "Ultrasound Computed Tomography" (UCT); unlike echo ultrasound that visualizes tissue interfaces, UCT measures the acoustic properties of the tissue (sound velocity and sound attenuation), and allows a quantitative image to be reconstructed. Greenleaf, J. F., S. A. Johnson, S. L. Lee, G. T. Herman, E. H. Wood, *Algebraic Reconstruction of Spatial Distributions of Acoustic Absorption Within Tissue from Their Two-Dimensional Acoustic Projections*. Acoustical Holography, 1974, 5: p. 591–603. Success with this modality was limited due to the limited availability of computational technology in the 1970s and Greeleaf et al., U.S. Pat. No. 4,105,018 titled Acoustic Examination, Material Characterization And Imaging Of The Internal Structure Of A Body By Measurement Of The Time-Of-Flight Of Acoustic Energy Therethrough specifically limited its technology to 2D ultrasound, at col. 8, line 47 to col. 9, line 1, stating that "[t]he advantage of cylindrical and circular cylindrical symmetry in ultrasound image formation is related to the basic property of all cylindrical surfaces; namely, that there is a translation or cylindrical axis. This means that if a cylindrical wave is generated it remains a cylindrical wave in a medium of constant index of refraction . . . This is equivalent to saying that in cylindrical symmetry each ray is contained in one and only one plane . . . Thus when using cylindrical waves the coupling of information between adjacent planes perpendicular to the cylinder axis is minimal or small compared to the coupling occurring with spherical waves. This is a great advantage and saves computer time since several small multi-plane problems are much easier to solve in total than one large multiple plane problem."

Currently, echo ultrasound is routinely used as an adjunct to X-ray mammography to determine the differentiation of simple cysts from solid masses. However, echo ultrasound cannot differentiate malignant and benign masses. Also, false positive X-ray mammograms result in a large numbers of unnecessary biopsies; in the United States approximately 75% of the million biopsies performed each year are benign. Thus, a non-invasive, specific, diagnostic modality such as the system of the present invention is needed.

Another use of the system of the present invention is as a screening modality, (to detect almost any lesion) this is the detection function that X-ray mammography is used. However, X-ray mammography misses 8 to 22% of palpable breast cancers. Standard echo ultrasound has not been proven effective for screening asymptomatic patients largely due to its inability to reliably detect microcalcifications. There is significant evidence in the literature that a UCT imager can be very sensitive for lesion detection. There has been great controversy over the starting age and frequency of X-ray mammographic screenings. This controversy arises mainly because of two limitations of mammography. The first is that mammography does not work well in dense breasts, which most young women have. The current recommendation is that most women start screening at age 40. However, 5% of breast cancers occur in women under 40. American Cancer Society, Surveillance Research, 1999. The second controversy is the potential risk of the cumulative effects of ionizing radiation. This worry has some doctors recommending mammographic screenings every two years. Since the most aggressive tumors need detection the earliest, frequent screenings are desirable. The UCT imager may not be able to detect microcalcifications, but it may still have utility as a screening modality in a select patient population in which mammography is not indicated.

A third potential utility of a 3D imager is for image-guided biopsies and surgical planning. The location, size, and stage of a lesion are parameters that are required for effective treatment planning. Therefore, the inventors feel that the optimal diagnostic strategy for the detection and diagnosis of breast abnormalities is a non-invasive imaging method that is not only highly accurate (both sensitive and specific) but also gives the size and 3D location of any lesion detected.

There are several other non-invasive modalities that may be used for screening and/or diagnosis of breast cancer including ultrasound (echo), Single Photon Emitted Computed Tomography (SPECT), Positron Emitted Tomography (PET) and Magnetic Resonance Imaging (MRI). MRI is very expensive and requires the injection of contrast agents to detect tumors. SPECT and PET are low-resolution modalities and require the injection of ionizing radiation. There are several newer technologies emerging (i.e. acoustical holography, infrared, electrical, optical, and elasticity methods) but none have yet proven to be the definitive methodology.

History of UCT

The allure of UCT for breast imaging is that it offers the potential to quantitatively image tissue properties. Most of the experimental work to develop an UCT imager was performed in the late 70's and early 80's. In spite of the limited technology available to these investigators, they showed promising results. For example, Greenleaf et al. achieved a sensitivity of 100% for palpable lesions with UCT for a small sample population. Greenleaf, J. F., R. C. Bahn, *Clinical Imaging with Transmissive Ultrasonic Computerized Tomography.* IEEE Transactions on Biomedical Engineering, 1981. BME-28(2): p. 177–185. Greenleaf et al. also showed that by combining the speed-of-sound with the patient's age and a measure of image texture that malignant and benign lesions could be differentiated. Greenleaf, J. F., R. C. Bahn, *Clinical Imaging with Transmissive Ultrasonic Computerized Tomography.* IEEE Transactions on Biomedical Engineering, 1981. BME-28(2): p. 177–185. Scherzinger et al. showed that by employing discriminant analysis, using combinations of speed-of-sound and attenuation in and around the lesion, one can accurately differentiate tissue types. Scherzinger, A. L., R. A. Belgam, P. A. Carson, C. R. Meyer, J. V. Sutherland, F. L. Bookstein, T. M. Silver, *Assessment of Ultrasonic Computed Tomography in Symptomatic Breast Patients by Discriminant Analysis.* Ultrasound in Med. and Biol., 1989. 15(1): p. 21–28. In a larger study (n=78), Schreiman et al. showed that a computer-aided diagnosis using UCT had a sensitivity of 82.5% for the diagnosis of a malignancy. Schreiman, J. S., J. J. Gisvold, J. F. Greenleaf, R. C. Bahn, *Ultrasound Transmission Computed Tomography of the Breast.* Radiology, 1984. 150: p. 523–530.

One of the main problems that these early investigators encountered was that they could not acquire enough projections (at least not quickly enough) to reconstruct an image without reconstruction artifacts. In a review article in 1993, Jones states that early investigators were often hindered due to the limited memory and processor speed of their current computers, which affected both image acquisition and reconstruction. Jones, H. W., *Recent Activity in Ultrasonic Tomography.* Ultrasonics, 1993. 31(5): p. 353–360. In addition, the length of time required to acquire a full study of the breast was too long to avoid patient motion and the resulting artifacts. This long imaging time was a byproduct of having to mechanically move the transducers to each scan position and the large number of projections required to reduce reconstruction artifacts. Greenleaf et al., using a specially designed UCT imager, took about 5 minutes to image 8 slices (4 slices at a time, each slice was 3 mm thick with a 7 mm gap between slices) in a clinical trial. In this clinical UCT prototype imager, 60 projections with 200 samples each were acquired, and the image reconstructed into a 128×128 matrix. Azhari et al. claim that the need for a large number of projections (i.e. 201 projections for a 128×128 pixel image) to reduce reconstruction artifacts makes standard UCT impractical for clinical use. Azhari, H., S. Stolarski, *Hybrid Ultrasonic Computed Tomography.* Computers and Biomedical Research, 1997. 30: p. 35–48. As recently as 1991, Jago and Whittingham, using a linear array to improve speed of acquisition, required approximately 2 minutes to acquire data for a 2D slice and an additional 2 hours to reconstruct a 64 by 64 matrix. Jago, J. R., T. A. Whittingham, *Experimental Studies in Transmission Ultrasound Computed Tomography.* Phys. Med. Biol., 1991. 36(11): p. 1515–1527. Andre et al. note that after the initial experimental research, most of the work on UCT, through the mid 1990's, was in theoretical reconstructions and not in experimental designs. Andre, M. P., H. S. Janee, P. J. Martin, G. P. Otto, B. A. Spivey, D. A. Palmer, *High-Speed Data Acquisition in a Diffraction Tomography System Employing Large-Scale Toroidal Arrays.* International Journal of Imaging Systems Technology, 1997. 8(1): p. 137–147. They attributed this trend to limited technologies and speculate that improved instrumentation has led to a renewed interest in UCT.

There are several limitations to UCT which arise from the behavior of sound as it transverses an inhomogeneous media. These include reflection, refraction, and diffraction. There are a number of methods in the literature to correct or account for these effects. Meyer et al. proposed a method to correct for multipath errors using a parametric multipath modeling and estimation technique. Meyer, C. R., T. L. Chenevert, P. L. Carson, *A Method for Reducing Multipath Artifacts in Ultrasonic Computed Tomography.* J. Acoust. Soc. Am., 1982. 72(3): p. 820–823. In a noiseless case, they showed an improvement in attenuation estimates. Pan and Liu proposed methods for correcting refractive errors. Pan, K. M., C. N. Liu, *Tomographic Reconstruction of Ultrasonic Attenuation with Correction for Refractive Errors.* IBM J. Res. Develop., 1981. 25(1): p. 71–82. They proposed to scan a small area around the straight line-of-sight and then use several different methods (i.e. maximum, sum, or average of the scan area) to measure attenuation. Chenevert et al. explored methods such as cross-correlation and phase-insensitive arrays. Chenevert, T. L., D. I. Bylski, P. L. Carson, P. H. Bland, D. D. Adler, R. M. Schmitt, *Ultrasonic Computed Tomography of the Breast.* Radiology, 1984. 152: p. 155–159; and Schmitt, R. M., C. R. Meyer, P. Carson, L, T. L. Chenevert, P. H. Bland, *Error Reduction in Through Transmission Tomography Using Large Receiving Arrays with Phase-Insensitive Signal Processing.* IEEE Transactions on Sonics and Ultrasonics, 1984. SU-31(4): p. 251–258. Cross-correlation minimizes the chance of noise being mistaken as the arrival of the received signal by comparing the signal to a water-path only signal. The use of a phase-insensitive array results in a better attenuation image, by accounting for refraction. Klepper et al. showed that reconstructing an image, where each pixel is the slope of attenuation vs. frequency, minimizes errors due to reflection and refraction. They used a range of frequencies from 3 MHz to 7 MHz and fit a straight line to the data. Klepper, J. R., G. H. Brandenburger, J. W. Mimbs, B. E. Sobel, J. G. Miller, *Application of Phase-Insensitive Detection and Frequency-Dependent Measurements to Computed Ultrasonic Attenuation Tomography.* IEEE Transactions on Biomedical Engineering, 1981. BME-28(2): p. 186–201. Greenleaf et al. also showed that the intercept of attenuation vs. frequency could be reconstructed. Greenleaf, J. F., R. C. Bahn, *Signal Processing Methods for Transmission Ultrasonic Comput-* erized Tomography. Ultrasonics Symposium Proceedings, 1980: p. 966–972. This is an image of reflection by structures larger than the wavelength and is highly correlated with back-scattered information imaged in B-mode scans.

Several investigators explored the use of ray-tracing, ray-linking and iterative reconstructions to generate more accurate images. Improvements in restoring macrostructural geometric proportions have been shown for object inhomogeneities of 5–10% (the breast has inhomogeneities of about 8%). These methods begin with a straight ray assumption to reconstruct an initial speed-of-sound image. Then ray-linking is used to create "new" projections, which are subsequently used to reconstruct a new image. This process is then iterated. Most of the ray-linking methods involve a technique called "shooting", iteratively searching for the initial angle of the ray from the transmitter that "hits" within some window around the receiver. These methods are computationally expensive and may not be possible to implement in a 3D imaging system.

Norton proposed an alternative method, which involves transforming the ray equation into an implicit integral equation satisfying the boundary conditions. These equations are then solved via successive approximations. Norton also proposed an explicit expression for the ray equation that is correct to the first order for refractive-index perturbations. Norton, S. J., *Computing Ray Trajectories Between Two Points: A Solution to the Ray-Linking Problem*. Optical Society of America, 1987. 4(10): p. 1919–1922. Andersen proposed an alternative technique based on rebinning of the projection data. Andersen, A. H., *A Ray Tracing Approach to Restoration and Resolution Enhancement in Experimental Ultrasound Tomography*. Ultrasonic Imaging, 1990. 12: p. 268–291; and Andersen, A. H., *Ray Linking for Computed Tomography by Rebinning of Projection Data*. J. Acoust. Soc. Am., 1987. 81(4): p. 1190–1192. In this technique, a new radial coordinate system is constructed passing through the center of the image. Rays are then projected from lines passing through the origin. A rebinning process is used and a new image reconstructed. This method is computationally less expensive than the brute force method typically used in ray-linking, a 60% timesavings. Andersen, A. H., *A Ray Tracing Approach to Restoration and Resolution Enhancement in Experimental Ultrasound Tomography*. Ultrasonic Imaging, 1990. 12: p. 268–291. We can extend the method of rebinning (center-out) to 3D in our reconstructions, detailed in the method of the present invention.

Diffraction Tomography

An alternative to geometrical acoustics for reconstruction is diffraction tomography, which often uses an approximation (Rytov or Born) to the wave equation to reconstruct images. These approximations are only valid in cases of weak scattering. Several investigators have experimented with diffraction imaging.

In order to obtain a linear approximation to the inhomogeneous wave equation, diffraction tomography is often based on the assumption of weak scatters. This assumption is not valid in the human breast due to highly refractive fat layers under the skin. One potential alternative involves the use of higher order approximations to the wave equation. Another alternative is to use iterative methods to solve the wave equation directly. Both of these alternatives are computationally very expensive. For example, the CPU time on a Cray computer was 2.5 hours to reconstruct a 200×200 pixel image from 200 projections. The reconstructed image was very accurate both qualitatively and quantitatively. Manry and Broschat showed that the incorporation of a priori information reduced the computation time by reducing the number of iterations approximately 40%, but the image becomes discretized to 3 grey levels. Manry, C. W. J., S. L. Broschat, *Inverse Imaging of the Breast with a Material Classification Technique*. J. Acoust. Soc. Am., 1998. 103(3): p. 1538–1546. Lu et al. have recently published a new method that involves the creation of a reconstruction method in a finite form utilizing a formal parameter. Lu, Z.-Q., C.-H. Tan, Z.-Y. Tao, Q. Xue, *Acoustical Diffraction Tomography in a Finite Form and Its Computer Simulations*. IEEE Transactions on Ultrasonics, Ferroelectrics, and Frequency Control, 2001. 48(4): p. 969–975. This method utilizes an approximation that is much less restrictive than those in the Born and Rytov approximations.

Much of the work in the area of diffraction tomography is also limited by the assumption that the object is being isonofied by a plane wave, which is not feasible in an imager. Sponheim, N., I. Johansen, *Experimental Results in Ultrasonic Tomography Using a Filtered Backpropagation Algorithm*. Ultrasonic Imaging, 1991. 13: p. 56–70. Sponheim and Johansen have suggested utilizing a reference wave as a first order correction. There is some theoretical work in which non-plane waves are used. Devaney and Beylkin developed a method for utilizing fan beam (spherical or cylindrical) isonofication for diffraction tomography and for the use of arbitrary transmitter and receiver configurations. Devaney, A. J., *Generalized Projection-Slice Theorem for Fan Beam Diffraction Tomography*. Ultrasonic Imaging, 1985. 7: p. 264–275; and Devaney, A. J., G. Beylkin, *Diffraction Tomography Using Arbitrary Transmitter and Receiver Surfaces*. Ultrasonic Imaging, 1984. 6: p. 181–193. Witten et al. included the effects of the transmitter beam pattern in their theoretical design of a practical 2D diffraction tomographer. Witten, A., J. Tuggle, R. C. Waag, *A Practical Approach to Ultrasonic Imaging Using Diffraction Tomography*. J. Acoust. Soc. Am, 1988. 83(4): p. 1645–1652. It is also interesting to note that they claim that any practical ultrasound based imager must use fixed transducers to eliminate errors due to vibrations and acquire data quickly enough to avoid artifacts due to patient motion. The inventors' clinical design meets these requirements.

Fast (approximately 3 sec per slice) 2D diffraction tomography systems with high-resolution (<1 mm in plane, but 10 mm thick slices) and the utilization of cylindrical waves have been previously developed. However, the systems result in nonisotropic voxels. Such a system is discussed in Andre, M. P., H. S. Janee, P. J. Martin, G. P. Otto, B. A. Spivey, D. A. Palmer, *High-Speed Data Acquisition in a Diffraction Tomography System Employing Large-Scale Toroidal Arrays*. International Journal of Imaging Systems Technology, 1997. 8(1): p. 137–147. Others have also experimented with a 2D system resulting in nonisotropic voxels; the system has an in-plane resolution of 0.5 mm; however, the slice thickness is again 10 mm. This system is discussed in Sponheim, N., I. Johansen, *Experimental Results in Ultrasonic Tomography Using a Filtered Backpropagation Algorithm*. Ultrasonic Imaging, 1991. 13: p. 56–70. Both of these experimental systems utilize first order Born or Rytov approximations.

Pixel/voxel number and size are also variables. Isotropic voxels (meaning same dimension in all three directions) is a feature of the present invention. The aforementioned systems do not have isotropic voxels: Many image modalities have good in-plane resolution but have thick slices. This creates partial volume error which is blurring of true tissue properties due to averaging of large sections of the tissue into one value that is displayed in an image.

Most diffraction tomography methods reconstruct only in 2D and thus the 3D scattering effect of the breast is a limiting factor of diffraction tomography, and has not previously been addressed in a practical imaging system. A 3D reconstruction algorithm for diffraction tomography utilizing a filtered back-projection algorithm on the Radon transform has recently reported in Anastasio, M. A., X. Pan, *Computationally Efficient and Statistically Robust Image Reconstruction in Three-Dimensional Diffraction Tomography*. J. Opt. Soc. Am. A, 2000. 17(3): p. 391–400. The method provides reconstruction that reduces to a series of 2D reconstructions over the 3D volume. This reconstruction is based on the Born or Rytov approximations.

Most of the work in diffraction tomography has been theoretical with few actual experimental devices being tested, and none in 3D. Diffraction tomography suffers from the weak scattering assumption, which is often employed, and is violated by strongly refracting fat layers. Note that phase aberration of ultrasound is not a function of breast size as explained in Trahey, G. E., P. D. Freiburger, L. F. Nock, D. C. Sullivan, *In Vivo Measurements of Ultrasonic Beam Distortion in the Breast*. Ultrasonic Imaging, 1991. 13: p. 71–90. This is suggestive that the major contributor to phase aberration is subcutaneous fat and not the internal structure of the breast. There have been similar findings in that examination of the wavefront amplitude profiles shows coherent interference, indicating refraction as the cause, as is explained in Zhu, Q., B. D. Steinberg, *Wavefront Amplitude Distribution in the Female Breast*. J. Acoustical Society of America, 1994. 96(1): p. 1–9. In addition, diffraction tomography is more computationally expensive than ray-based UCT and may be limited by the discrete implementation of the reconstruction process. Therefore, diffraction-based reconstructions is not preferred for use in the present invention. Rather, in the present invention, use of geometrical acoustics, with ray tracing to correct for the refraction caused by subcutaneous fat is preferred.

Ultrasound Tissue Characterization

There has been work both in vivo and ex vivo on trying to characterize the ultrasound characteristics of breast tissue. The results of this work suggest that if an imager were accurate, the speed-of-sound and the attenuation-of-sound could be combined with specialized statistical methods to differentiate tissue types in vivo.

It has been shown that the average speed-of-sound in the breast is 1510 m/s for pre-menopausal women and the speed of sound decreases to 1468 m/s in postmenopausal women. Kossoff, G., E. K. Fry, J. Jellins, *Average Velocity of Ultrasound in the Human Female Breast*. The Journal of the Acoustical Society of America, 1973. 53(6): p. 1730–1736. The difference was attributed to the increase in fat in the breast, post-menopause. Yang et al., using very precise techniques, showed in a very small sampling of excised tissue that the mean speed-of-sound in malignant tissue was 1560 m/s while the surrounding normal tissue had speeds ranging from 1404 to 1450 m/s. Yang, J. N., A. D. Murphy, E. L. Madsen, J. A. Zagzebski, K. W. Gilchrist, G. R. Frank, M. C. Mcdonald, C. A. Millard, A. Faraggi, C. A. Jaramillo, F. R. Gosset, *A Method for In Vitro Mapping of Ultrasonic Speed and Density in Breast Tissue*. Ultrasonic Imaging, 1991. 13: p. 91–109.

Arditi et al. in excised pig mammary tissue showed that insertion loss was linear vs. frequency over the range of 2 to 9 MHz. Arditi, M., P. D. Ecmonds, J. f. Jensen, C. L. Mortensen, W. C. Ross, P. Schattner, D. N. Stephens, W. Vinzant, *Apparatus for Ultrasound Tissue Characterization of Excised Specimens*. Ultrasonic Imaging, 1991. 13: p. 280–297. Landini et al. showed that the slope of attenuation vs. frequency was able to distinguish malignant lesions with productive fibrosis. Landini, L., R. Sarnelli, F. Squartini, *Frequncy-Dependent Attenuation in Breast Tissue Characterization*. Ultrasound in Med. & Biol., 1985. 11(4): p. 599–603. Berger et al. have shown that the slope of attenuation vs. frequency is dependant on the genital life of the patient. Berger, G., P. Laugier, J. C. Thalabard, J. Perrin, *Global Breast Attenuation: Control Group and Benign Breast Diseases*. Ultrasonic Imaging, 1990. 12: p. 47–57. Edmonds et al. showed that in excised breast tissue the speed-of-sound had the best distinguishing power and that the use of Classification And Regression Trees (CART) aids in tissue differentiation. Edmonds, P. D., C. L. Mortensen, J. R. Hill, S. K. Holland, J. F. Jensen, P. Schattner, A. D. Valdes, *Ultrasound Tissue Characterization of Breast Biopsy Specimens*. Ultrasonic Imaging, 1991. 13: p. 162–185.

Scherzinger et al., Greenleaf et al., Glover, and Schreiman et al. have all had some success in discriminating tissue types in vivo using 2D UCT and often employing computer-assisted classifications, in spite of the fact that there is overlap of ultrasound properties between tissue types. Glover, G. H., *Computerized Time-of-Flight Ultrasonic Tomography for Breast Examination*. Ultrasound Med. Biol., 1977. 3: p. 117–127; Scherzinger, A. L., R. A. Belgam, P. A. Carson, C. R. Meyer, J. V. Sutherland, F. L. Bookstein, T. M. Silver, *Assessment of Ultrasonic Computed Tomography in Symptomatic Breast Patients by Discriminant Analysis*. Ultrasound in Med. and Biol., 1989. 15(1): p. 21–28; Schreiman, J. S., J. J. Gisvold, J. F. Greenleaf, R. C. Bahn, *Ultrasound Transmission Computed Tomography of the Breast*. Radiology, 1984. 150: p. 523–530.

Because there is overlap between the speed-of-sound and attenuation for normal and malignant tissue, the use of other parameters may be needed to differentiate tissue. These may include: backscatter coefficient, the acoustic nonlinearity parameter (B/A), temperature dependence of the speed-of-sound and attenuation, quantification of the anisotropy of the ultrasonic tissue properties, as well as, various combinations of all these parameters. The design of the present invention allows the acquisition of these parameters with only slight modifications.

Limitations of Early 2D UCT and Proposed Solutions

Although early 2D UCT imagers showed promise for use as an adjunct diagnostic exam, they were not accepted clinically for several reasons. The first was the technical limitations which 1) limited the number of projections that could be acquired in a reasonable time (created reconstruction artifacts), 2) created long reconstruction times, prohibiting the extension of methods to 3D, and 3) limited computer analysis of the images. The inventors' prototype overcomes these problems by acquiring a 3D image in approximately 120 sec, uses current computational power to reconstruct a 3D image, and creates a digital image, which allows for easy implementation of computerized image analysis.

The second limitation is that the effects of refraction and diffraction are 3D phenomena and have previously only been addressed in 2D. Again, one goal is to create a 3D UCT imager specifically to correct for 3D refraction.

The present invention overcomes the disadvantages of prior imaging modalities by providing in one embodiment a 3D UCT imager using a cylindrical array of small piezo-electric elements acting as both transmitters and receivers. This arrangement allows for quick collection of 3D projections (preferably in a cone beam fashion). Specifically, projections can be created between any pair of piezoelectric elements that are lining the image chamber. This geometry creates a cone beam acquisition. In 2D imaging, fan beam acquisition refers to the case where the rays spread from a source like a fan. This configuration creates non-parallel projections. Cone beam is an extension of fan beam acquisition to the 3D case. Thus, the rays spread from a source to create a set of projections shaped like a cone. By utilizing a hemispherical transmission, the present invention, in effect, is a special case of cone beam acquisition, i.e. the acquisition scheme utilizes non-parallel projections. In typical cone beam acquisition, like the configuration used in X-ray computed tomography, a 2D flat surface of receivers is used. In the configuration of at least one embodiment of the present invention, the receivers are on a cylinder. 3D reconstruction will result in true 3D images. The advantages of the 3D UCT imaging system of the present invention are numerous and include: 1) the absence of ionizing radiation, 2) the ability to provide true 3D acquisition, reconstruction, and display, 3) the ability to quantify tissue properties, and thus, differentiate malignant and benign tissue to avoid the need for an invasive biopsy, 4) the ability to image dense breast tissue typically found in young women (i.e. women age 40 or less); 5) the availability of the system for use in frequent follow-up imaging for determination of efficacy of treatment because of the absence of ionizing radiation; and 6) the ability to provide a comparatively comfortable modality, as there is no need for compression of breast tissue when using the system. In addition to the stated advantages, the image created by the system of the present invention is created in a digital format, and has advantages typical of digital image formats, including the use of the 3D digital image with computer aided diagnosis and telemedicine.

SUMMARY OF THE INVENTION

The present invention is an apparatus for forming an ultrasound image of a target, including an imaging chamber having a plurality of cylindrical rings. The plurality of cylindrical rings are stacked in a vertical arrangement within an interior of the imaging chamber. Each of the cylindrical rings includes a plurality of omni-directional transceivers mounted thereon. The apparatus also includes a controller coupled to each of the omni-directional transceivers for selectively activating one of the omni-directional transceivers to transmit an acoustic wave at the target and a predetermined number of the omni-directional transceivers to receive acoustic waves propagated through the target. At least two of the receiving transceivers are on a different cylindrical ring such that the received acoustic waves form a cone-shaped beam. The apparatus also includes an imaging processing unit coupled to the plurality of omni-directional transceivers for processing the cone-shaped beam and for constructing a three-dimensional image of said target therefrom, and a display coupled to the image processing unit for exhibiting the three-dimensional image of the target.

DESCRIPTION OF THE DRAWINGS

In describing the present invention, features of the invention are not necessarily shown to scale. Also, reference will be made herein to FIGS. 1–4 of the drawings in which like numerals refer to like features of the invention and in which:

FIG. 2b is a perspective view of a cylinder and including a description of the cylinder volume formula that can be used to calculate the volume of the imaging chamber of FIG. 2a.

DESCRIPTION OF PREFERRED EMBODIMENTS OF THE INVENTION

Computer System

Figure 1A:
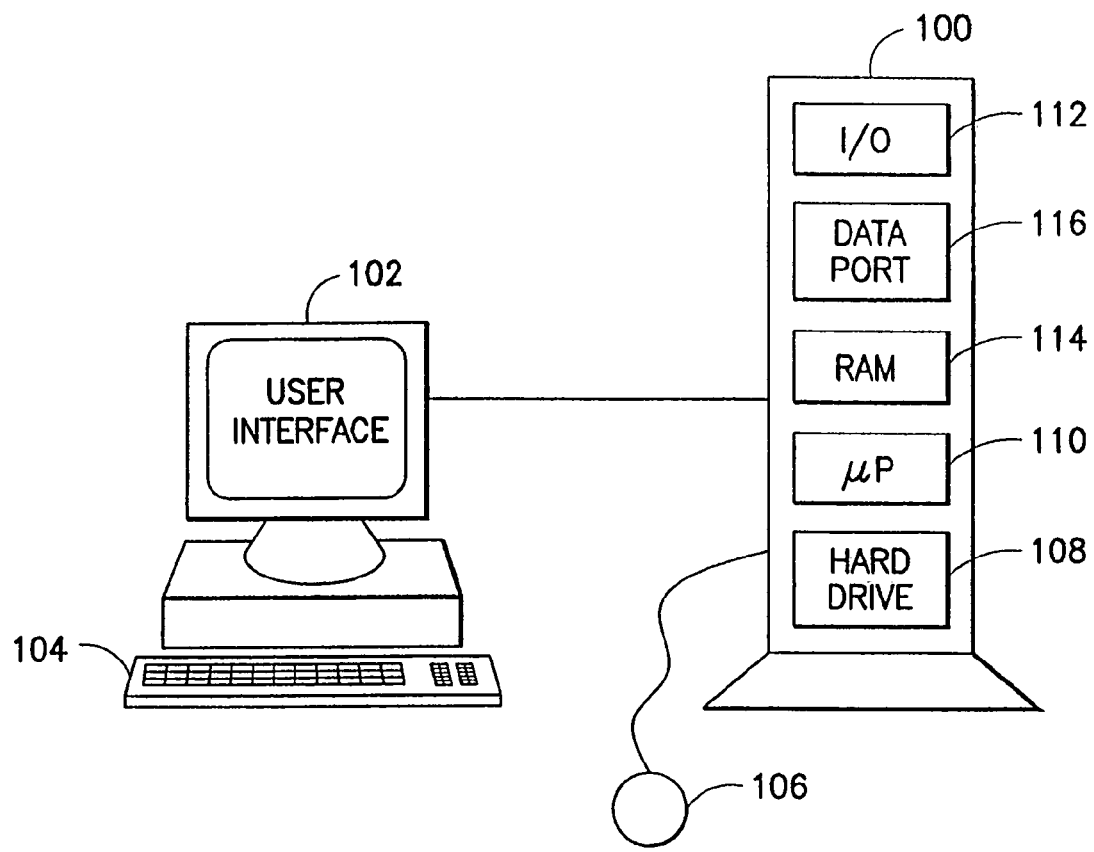
FIG. 1a is a block diagram of a microprocessor based computer system that may be part of the imaging system of the present invention.

FIG. 1a is a block diagram of a microprocessor based computer system 100 that may be part of the imaging system 10 of the present invention. Computer system 100 may be a personal computer which is used generically and refers to present and future microprocessing systems with at least one processor operatively coupled to a user interface means, such as a display 102 and keyboard 104, and/or a cursor control, such as a mouse or a trackball 106 or other input device. The computer system 100 may be a workstation that is accessible by more than one user. The personal computer also includes a conventional processor 110, such as a Pentium® microprocessor manufactured by Intel, data ports including but not limited to USB Ports 116 and conventional memory devices such as hard drive 108, floppy drive 112, and RAM 114.

3D Ultrasound System

Figures 1, 1B:
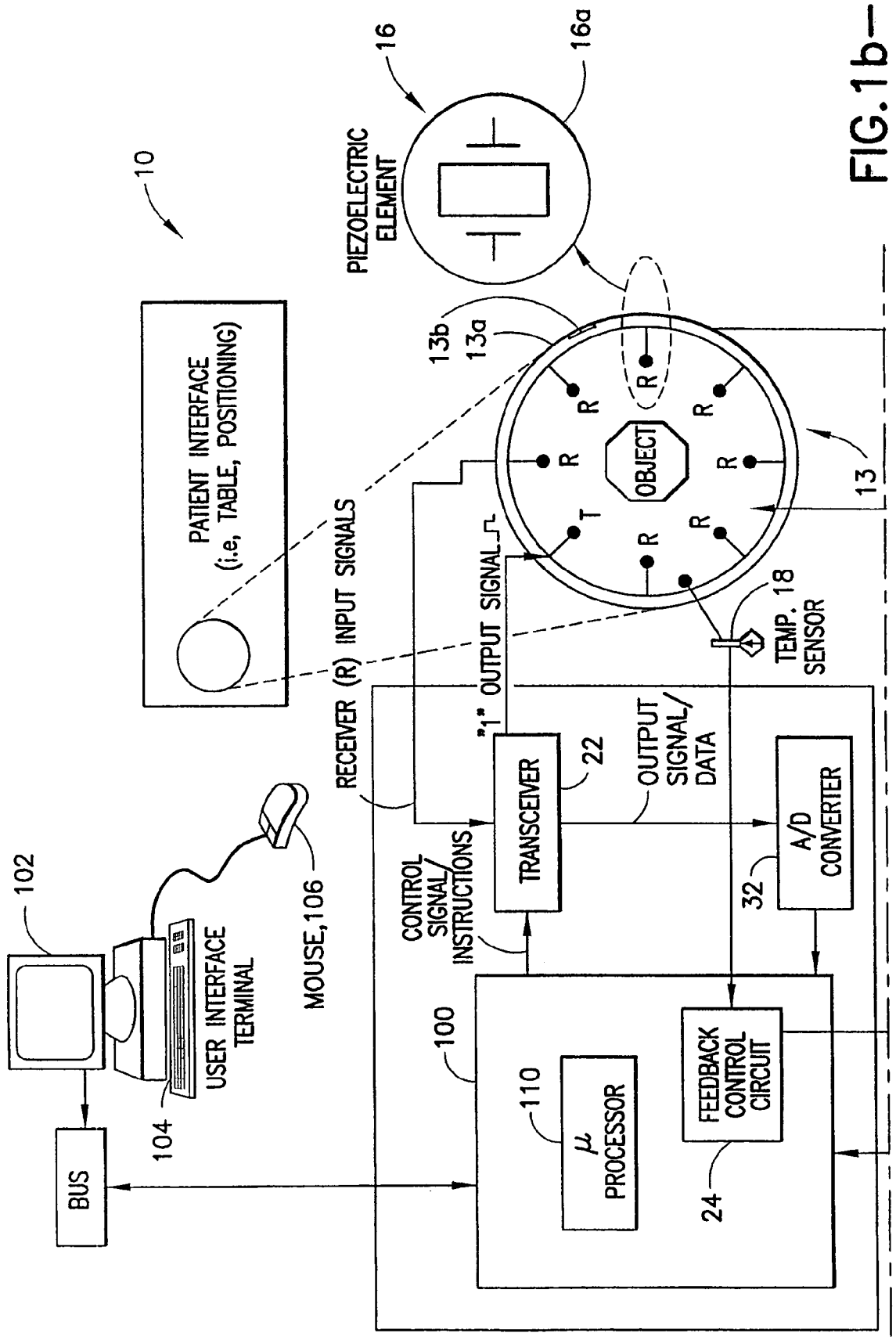
FIGS. 1b and 1c are block diagrams of embodiments of the system of the present invention.
Figure 1C:
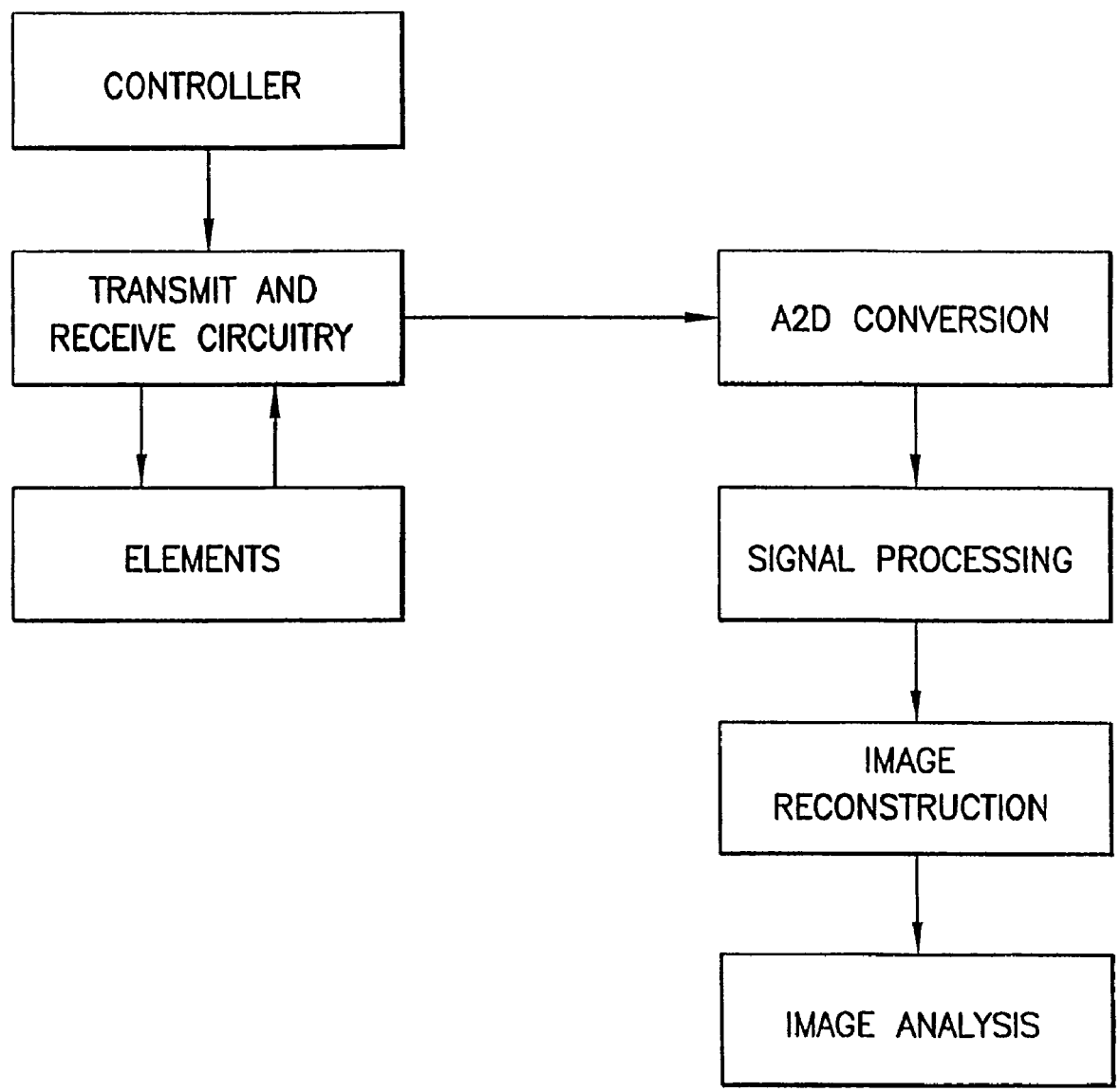

FIG. 1b is a block diagram of an embodiment of the system 10 of the present invention. The system 10 comprises an anechoic, fluid filled chamber 12, essentially free from echoes and reverberations; the chamber 12 is also referred to herein as an imaging chamber 12. Imaging chamber 12 comprises two or more rings 14 including a plurality of piezoelectric elements 16 mounted thereon. The imaging chamber 12 is described in further detail in the description of FIG. 2a, below. The system 10 is operatively connected to various elements the operation of which are also described below.

The elements of system 10 include a control system 100 (also referred to herein as computer 100 or personal computer 100). The control system 100 is operatively coupled to a temperature sensor 18 which preferably operates in a feedback control circuit as part of control system 100 to control heating/cooling unit 20. The feedback control circuit is generally denoted as element 24 of control system 100. One of ordinary skill in the art would be familiar with the components of a feedback control system and therefore, so as not to obscure the description of the present invention, the details are not described herein. The heating/cooling unit 20 performs the operation of increasing or decreasing the temperature of a liquid that is in the imaging chamber 12.

Variation of temperature affects the movement of sound waves in the imaging chamber 12 and is discussed below.

In addition to the temperature feedback control circuit 24, the imaging system 10 also comprises a transmitter/receiver unit 22, also referred to herein as transceiver 22, which is capable of receiving multiple input signals, one from each of the piezoelectric elements 16 and is also capable of providing an input, preferably an impulse, to one of the piezoelectric elements 16 which acts as an omnidirectional (or hemispherical) transmitter. The other piezoelectric elements 16 acting as receivers also use omnidirectionality. Further details of the transmit/receive unit 22 of the system 10 are explained below including the output to analog to digital converter 32.

It should be noted that the system 10 of the present invention, as shown in FIG. 1b illustrates only one ring and therefore does not reflect the ability of the imaging chamber to provide data for reconstructing a three-dimensional image. One ring 14 is shown at imaging chamber 12 as a top view for the sake of simplicity in illustrating an embodiment of the imaging system 10 configurations. With respect to the configuration of the imaging system 10, one of ordinary skill in the art would recognize that various components shown separately in the illustration of FIG. 1b could be combined into a single unit or other configuration convenient to performing the system 10. For example, the individual control system and signal processing components can be commercially available individual components that are interconnected manually or alternately some of the components could be designed and manufactured into a single aesthetically pleasing, pre-connected, integrated package (shown for example, by dotted lines around the following electronic components: transceiver 22, feedback control circuit 24, analog to digital converter 32, control system 100 and microprocessor 110.

The patient interface table can reduce the actual time of a screening scan; time is largely dependent on the design of the table housing the imager. Patient positioning can be the most time consuming component. With this design consideration in mind, screening scans should take no more than 5–10 min. for both breasts. The table preferably has one center opening and is hydraulically adjustable. The other important component is to design a table (some modification to a biopsy table), which not only houses the imager, but is also comfortable and ergonomically correct for the patient. It can need to allow for easy patient positioning, taking into account potential physical limitations of some patients. It can probably use hydraulics to lower the patient into position.

The imaging system 10 of the present invention can also include a server 26 for storage of data. This is a preferred arrangement for storing data, because the data could be accessed from the server 26 via a computer system such as a networked personal computer 28 connected to the network via a local area network (LAN) connection 30 or other suitable configuration. The server 26 arrangement is also preferred because of the ability to store large quantities of data and because of its accessibility via network connection. However, the data could be stored on the storage drive 108, shown in FIG. 1a; or on other storage media such as, for example, writable DVD or CDROM (not shown), however in this configuration, the amount of data storage available and access to the data would be limited as compared to the server configuration.

Specific features of the imaging chamber 12 are described below in the description of FIG. 2a including pump 33, drain 34, omni-directional (or hemispherical) piezoelectric elements 16 and acoustic absorbing material 36. Further details of the piezoelectric element are explained below in the description of FIGS. 2c–2e.

Imaging Chamber

Figure 2A:
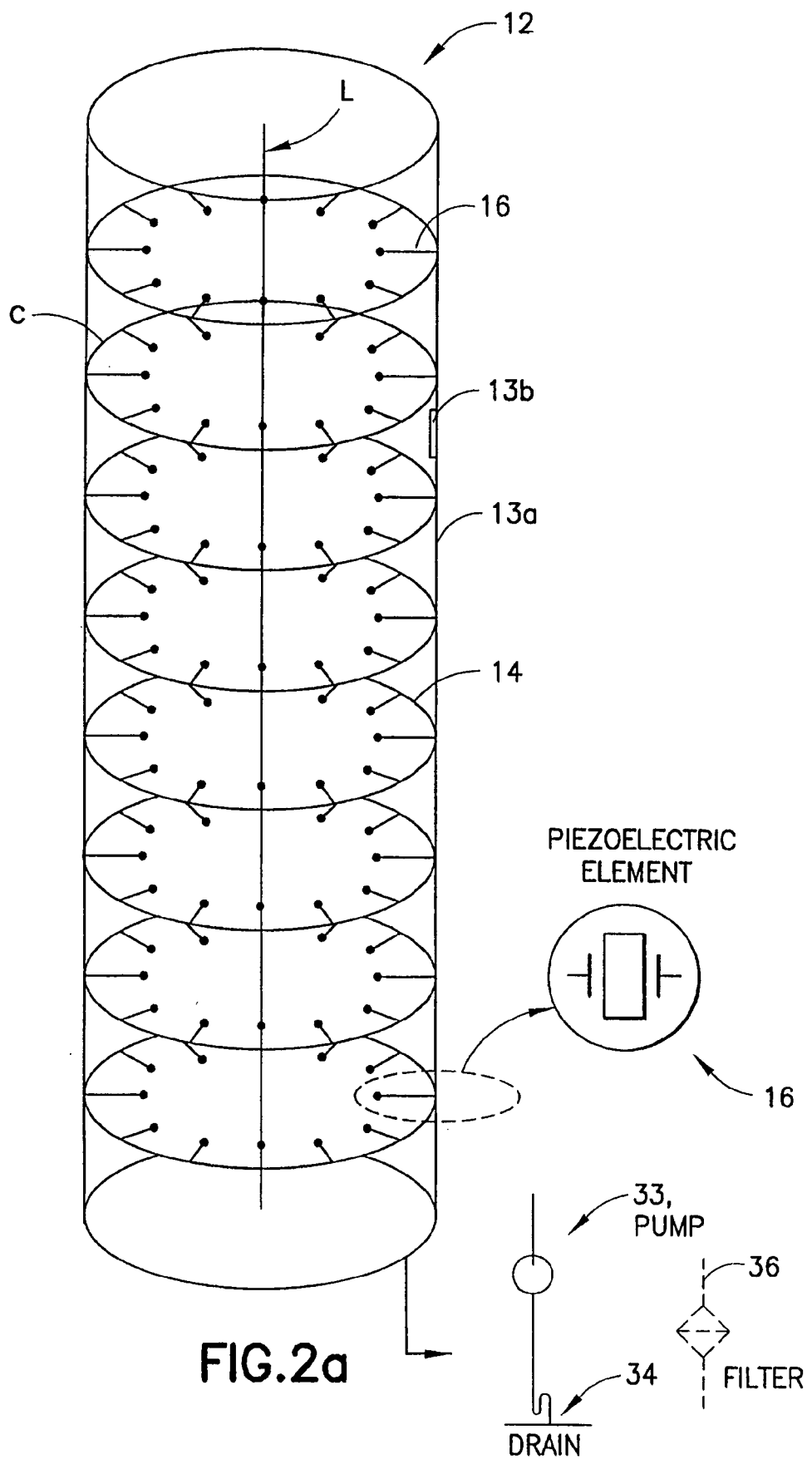
FIG. 2a is a perspective view of an embodiment of an imaging chamber of the system of the present invention.

FIG. 2a is a perspective view of an embodiment of an imaging chamber of the system of the present invention. The imaging chamber 12 of FIG. 2a comprises, in the present embodiment, a cylinder 13 comprising cylinder wall 13a and an acoustic (sound absorbing) coating 13b, and eight rings 14 of piezoelectric elements 16 disposed within the cylinder wall 13a and spaced apart from one another as explained herein. For simplicity of the drawing, the acoustic coating is shown on only a small portion of the cylinder wall 13a interior in FIG. 2a. However, the acoustic coating covers substantially the entire portion of the interior wall 13a of cylinder 12. The acoustic coating is preferably an acoustic absorbing material such as ρc ("rho") rubber which has an acoustic impedance which is matched to the fluid filling the chamber and has a high attenuation coefficient in order to quickly attenuate the ultrasound. The acoustic coating is important because upon the initiation of a new transmission, the sound from the previous transmission needs to be damped. The amount of time needed for the echo to damp is about three times the time it takes sound to travel the distance between the transmitter and the receiver farthest from the transmitter in the back-ground fluid.

Each of the eight rings comprises piezoelectric elements 16 of approximately 2 mm in diameter that each act to transmit or receive signals as instructed by control system 100 and transceiver unit 22. The preferred piezoelectric elements 16 are 2 mm omnidirectional piezoelectric elements manufactured by Sonometrics Corporation of London, Ontario, Canada. The preferred piezoelectric element 16 can act as both a transmitter T or a receiver R depending upon the input signal received by the piezoelectric element 16. The piezoelectric element commonly referred to as a piezoelectric crystal acts as a transmitter when the piezo material is subjected to a voltage causing mechanical stress on the piezo material. Conversely, the piezoelectric crystal acts as a receiver and will generate a voltage when mechanical pressure is applied. The mechanical pressure created by the system of the present invention is caused by sound waves created by piezoelectric transmitter element 16T. The sound waves move fluid in imaging chamber 12; the fluid applies pressure onto the piezoelectric receiver elements 16R. Those piezoelectric elements 16 are illustrated with various details in FIGS. 2c, 2d, 2e, 2f and 2g described below.

The imaging chamber 12 includes a means for changing or cleaning the fluid contained therein. This can be attained by either a pump and drain system for quickly removing used fluid. Alternately the fluid can be filtered between use on patients so as to not spread contaminants.

The preferred fluid for use in the imaging chamber 12 is saline because saline closely matches the refractive index of the human body and therefore bending is reduced.

In the interest of simplicity, the apparatus of FIG. 2a illustrates only twelve piezoelectric elements 16 per ring 14 whereas empirical data has been gathered using an apparatus comprising thirty-two piezoelectric elements 16 per ring. Each of the thirty-two piezoelectric elements 16 mounted in each of the eight rings 14 are substantially equally spaced (about every 11.25° calculated by dividing 360° by the number of piezoelectric elements i.e. 360÷32) piezoelectric elements 16 around the circumference C of the rings 14. A ring of piezoelectric elements can be place at about every 4 mm along the long axis L (shown with a dotted line in FIG. 1a) of the chamber. Therefore, a total of 256 piezoelectric elements can be positioned in the chamber in eight separate rings of piezoelectric elements (8 rings×32 piezoelectric elements=256 piezoelectric elements in the chamber). The elements transmit (pulsed) at high frequencies (6 MHz or 8 MHz) to minimize diffractive effects and can be arranged in an alternating pattern (n=16 for each frequency) around each ring. The chamber can rotate about its axis to allow each frequency to be measured from a multiplicity of identical locations. Note that each frequency can be measured at each location. These frequencies are high enough to minimize diffractive effects and still be able to penetrate the breast. While parameters including, but not limited to, volume, height, diameter, size, spacing, and other specific numerical data are disclosed in the present embodiment, the specific configuration is given as an example and is not meant to limit the invention to the specific parameters disclosed. Other configurations could be determined by one of ordinary skill in the art.

Imaging Chamber Design

We have found no evidence in the literature that anyone has attempted a 3D UCT imager. In 1987, Greenleaf wrote, "Since the morphology of the breast is highly complex and three dimensional, it may be that three-dimensional images (from UCT) would improve the capabilities of diagnostic methods . . . Three-dimensional images of other characteristics, such as speed and attenuation, may also improve the ability to evaluate the spatial morphologic character of breast architecture in health and disease". Thus, based on the evidence in the literature that 1) 2D UCT has shown promise for in vivo tissue classification and 2) that all 2D implementations of UCT, including those using diffraction tomography, have thus far failed to be accepted clinically, a 3D UCT imaging system of the present invention is needed.

A prototype imaging chamber can be made Plexiglas to provide a framework for a cylindrical array of small piezoelectric elements. The elements can be displaced from the walls of the chamber by small spacers (1 cm in length) in order to minimize any errors due to reflections off of the chamber walls. The rest of the chamber walls can be lined preferably with 0.75 cm of ρc rubber to produce an anechoic environment. The resulting "effective" imaging chamber dimensions can be 128 mm in diameter and 32 mm high.

Greenleaf had proposed a circular design for a UCT imager because of the advantages of 1) cylindrical geometry, 2) no mechanical motion required, and 3) the creation of a fan-beam configuration. The imaging system of the present invention has the additional advantage of a 3D cone-beam configuration. 3D projection data can be acquired simultaneously, and very little mechanical motion is required. The ability to remove motion can also improve the image quality of tomographic imaging. In typical 2D UCT imagers, the source and receiver are moved around the object to be imaged. Sponheim and Johansen state that the positioning of the source and receiver should be known to within fractions of a wavelength to prevent image blurring. This is on the order of tens of micrometers for most 2D UCT imagers. This precise machining is feasible but can be quite costly for high-speed acquisition. In prototype imaging chamber 12, small rotations of the entire image chamber can be performed in order to image each individual frequency from the same sixty-four locations, allowing for fast imaging time and easier machining (since the piezoelectric elements 16 remain in a fixed relationship to each other during each rotation). This configuration creates approximately the same number of projections (in each 2D plane) as if there were 256 elements (128 of each frequency) per ring, the number of elements estimated for a clinical imager. The prototype design allows testing of the criteria at a reasonable current cost but is too small and too slow for use clinically. It has been estimated that a complete 3D data set from all 256 crystals, each in 64 positions, can be acquired in approximately 120 seconds (most of this time is to allow for rotation of the chamber, the actual imaging time would be approximately 20 sec).

Small (2 mm diameter) piezoelectric elements, which have a fast response time, can be used to accurately measure transit-time. This small element size also minimizes phase-cancellation errors. These elements can emit and receive ultrasound omni-directionally by means of a spherical lens of epoxy 16a (epoxy coating, see FIG. 2c).

Heat

We can also create an isothermic chamber to minimize the effects of temperature on the speed-of-sound. We can use a separate heated water bath to maintain the water temperature at 37° C. A set of tubes can run from the heated bath to a series of valves located near the top of the imaging chamber to fill the tank with water just prior to imaging. The tank can drain back to the heated tank upon completion of imaging. We can create a filtration system for use with patients. The exterior of the chamber can be insulated to minimize heat loss during imaging. If temperature dependence of ultrasound-based tissue parameters is discovered to be useful this design is easily modified to image at temperatures other than 37° C.

Figure 2B:
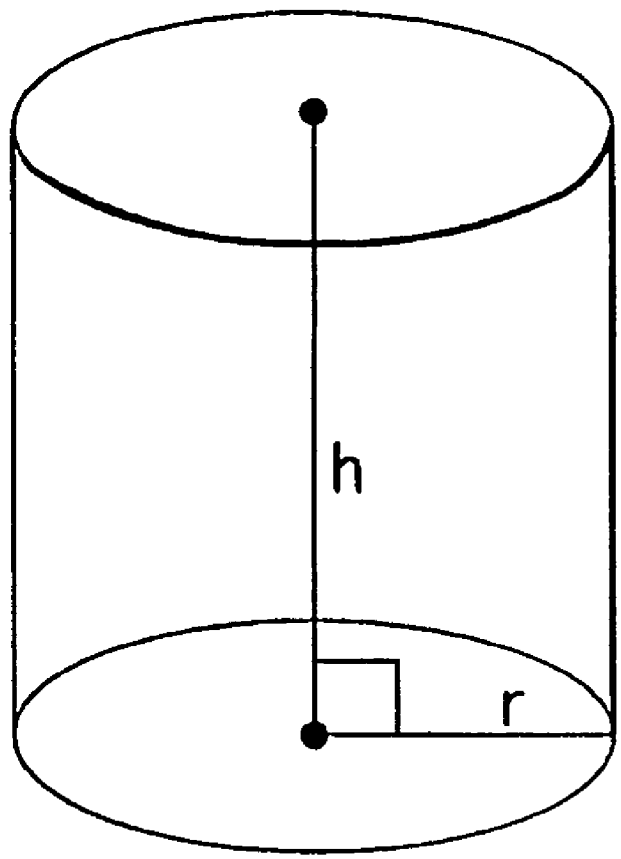

Returning to the embodiment of FIG. 2a (not to scale), the 3D ultrasound imaging chamber 12 of the system 10 of the present invention has an effective imaging volume of 4.12 kl which is calculated using the cylinder volume formula illustrated in FIG. 2b. The cylinder of the apparatus of the present embodiment is about 32 mm high and has a diameter of about 128 mm. The formula and calculation of volume for the present example is as follows:

$$V = \pi r^2 h \text{ or } V = \pi (d/2)^2 h$$

$$V = \pi (12.8 \text{ cm}/2)^2 3.2 \text{ cm}$$

$$V = 4.12 \text{ kl}$$

It should be noted that the measurements explained herein correlate to prototype dimensions; however, the preferred embodiment of the clinical system is planned to have a diameter of about 256 mm to accommodate a human breast and a height of about 256 mm. Other dimensions could be used as determined by one of ordinary skill in the art considering factors such as for example, the application of the system, the size and material of the object to be imaged, the number and size of piezoelectric elements, and the transmission frequency being employed.

Figure 2C:
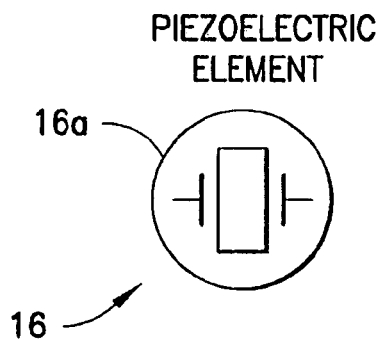
FIG. 2c is a schematic representation of a piezoelectric element and also illustrating a coating around the piezoelectric element.
Figure 2D:
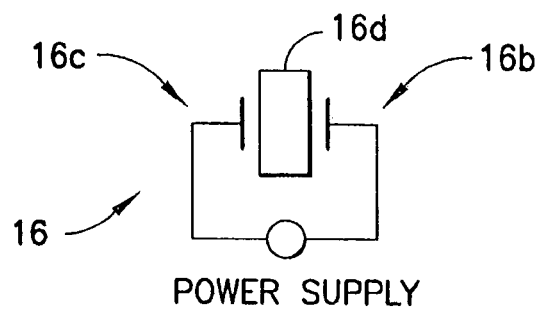
FIG. 2d is another schematic representation of the piezoelectric element including a power supply connected to the element.
Figures 2E, 2F:
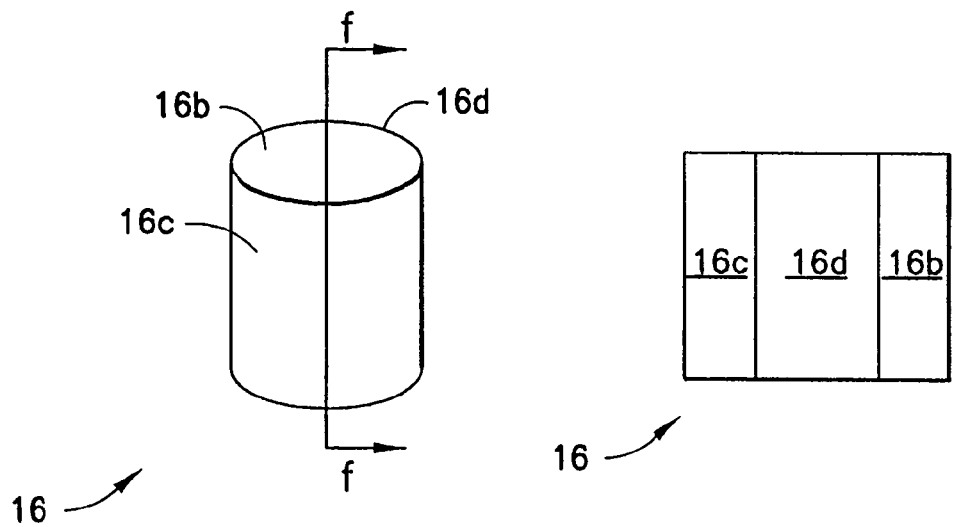
FIG. 2e is perspective view of the piezoelectric element illustrating the piezo material and capacitive plating.
FIG. 2f is a cross sectional view of piezoelectric element 16 along line f—f of FIG. 2e.
Figure 2G:
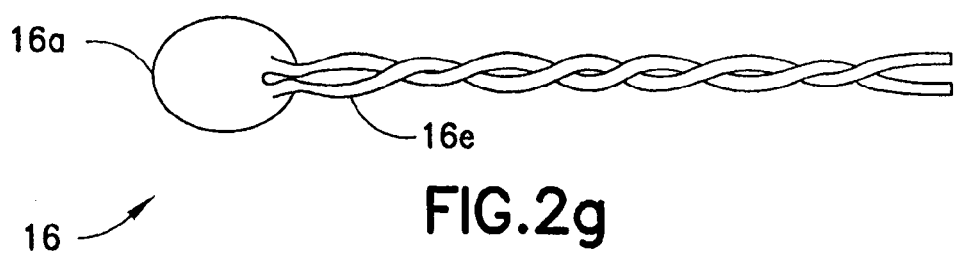
FIG. 2g is an illustration of a 2 mm omni-directional piezoelectric element.

A schematic representation of piezoelectric element 16 of FIG. 1b is shown in FIG. 2c as indicated by the ellipses around the piezoelectric element 16 and the arrow pointing to the FIG. 2c schematic representation of the piezoelectric element 16. FIG. 2c also illustrates an epoxy coating 16a around the piezoelectric element 16. The piezoelectric elements 16 are illustrated with various detail in FIGS. 2c, 2d, 2e, 2f and 2g. FIG. 2d is another schematic representation of the piezoelectric element including a power supply connected to the element 16. The piezoelectric element 16 comprises capacitors 16b and 16c as well as piezo material 16d (i.e. ceramic or crystal). FIG. 2e is a perspective view of the piezoelectric element illustrating the piezo material 16d and capacitive plating 16b and 16c. FIG. 2f is a cross sectional view of piezoelectric element 16 along line f—f of FIG. 2e. FIG. 2g is an illustration of a 2 mm omnidirectional piezoelectric element 16.

Method

Figure 3:
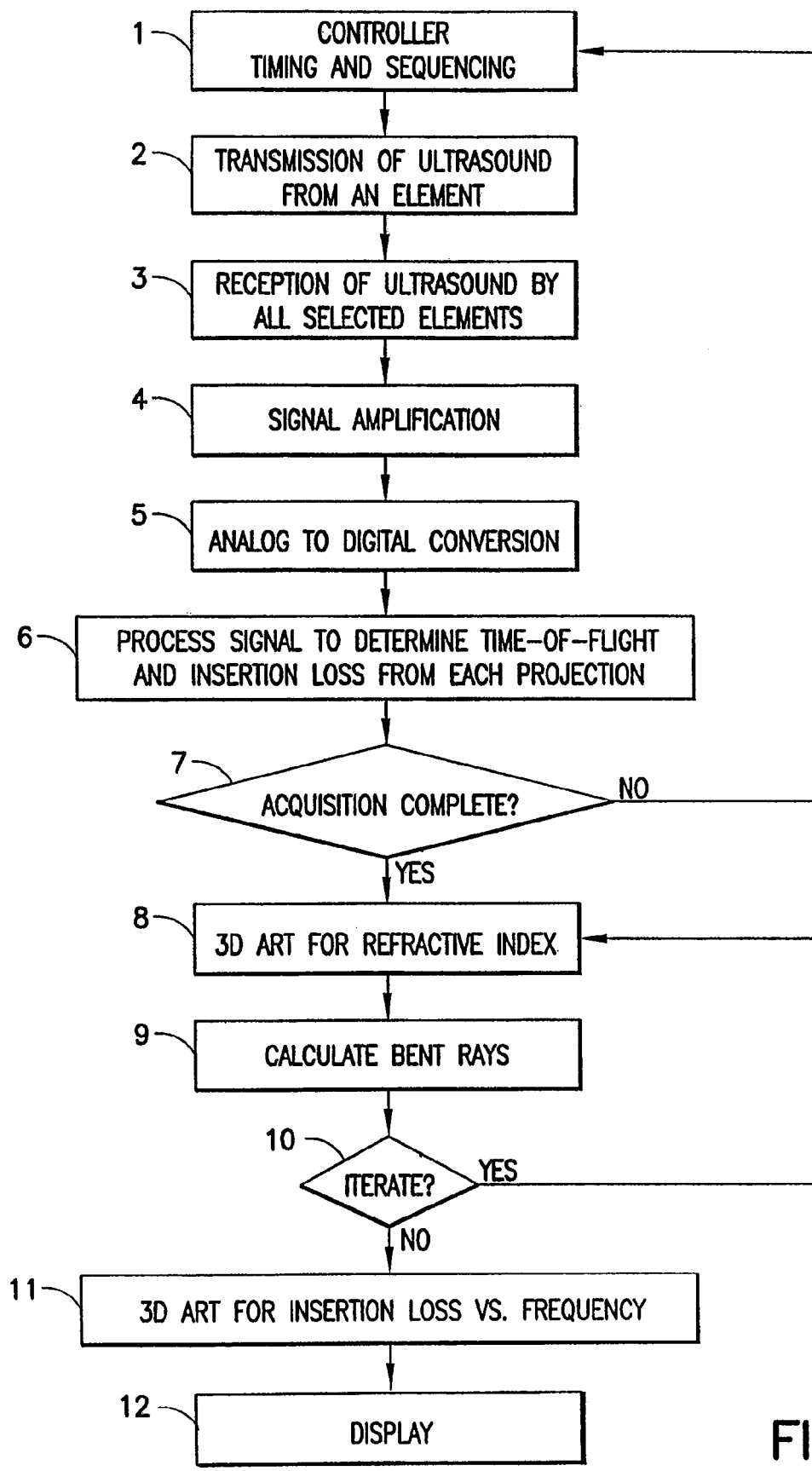
FIG. 3 is a flow chart of an embodiment of a method of the present invention.

FIG. 3 is a flow chart of an embodiment of a method of the present invention. The method is described in the number descriptions corresponding to the flow chart as follows:

1. Controller-Timing and Sequencing

Each element, in turn, is selected to be the transmitter with the remaining elements designated to act as receivers. The timing of each transmission is also determined.

2. Transmission

An input waveform, preferably an impulse signal, is applied to the transmitting element. This creates a wave front, which then propagates through the image chamber and test object.

3. Reception

As the wave front reaches each receiving element, the element is excited generating an electrical signal.

4. Signal Amplification

The received electrical is amplified using standard methods.

5. Analog to Digital Conversion

The amplified analog signals are then digitized using a high-speed analog-to-digital converter at a sampling rate much greater than the Nyquist Sampling Rate.

6. Process Signal

Transit-time is determined for each projection, the ray connecting each receiver to the transmitter. It is crucial that transit-time measurements be done precisely so that the ultimate, quantitative, reconstructed image accurately reflects the true tissue properties. The simplest method for detection of the ultrasonic pulse at the receiving transducer is based on a single threshold. This "leading edge" technique detects a pulse when the signal exceeds a threshold that is set above the noise level. Since the earliest part of the pulse is likely to follow the straightest path, detection based on the leading edge can minimize the effects of refraction. This approach is straightforward to implement and can be used as an initial basis for comparison. However, low amplitude signals from high speed-of-sound regions can distort the measurement if they exceed the threshold.

A more effective method of pulse detection may be to use cross-correlation. Here, the pulse waveform is acquired and compared to a reference pulse that was acquired in water. The transit-time is determined by matching the acquired signal to the reference signal. The offset that best matches according to a cross-correlation gives the transit-time. No threshold needs to be set, and therefore, small amplitude signals cannot confound the detection. In practice, further refinements may be necessary including repeat measurements and spatial averaging of transit-times. Note however, that simple thresholding may be superior in cases of high attenuation.

Insertion loss is also calculated for each projection. Insertion loss is defined as the difference in received energy between a background-fluid only received signal and the received signal after an object has been placed in the chamber. Insertion loss is really the sum of all energy loss from true attenuation, diffraction, refraction and reflection.

7. Acquisition Complete?

Have all elements transmitted?

8. 3D Simultaneous Algebraic Reconstructive Technique (SART) for Refractive Index For SART-type reconstructions, a linear algebraic solution is determined. Here, WP=Q, where P is the image vector, Q is the projection (measurement) vector, and W is the weight matrix. W is determined by computing the length of the ray segment crossing each voxel for each ray. Voxels outside of the cylinder can be constrained to be zero. The system may be over constrained and a least-squares solution (pseudo-inverse) for P applied. The inventors can develop a 3D simultaneous algebraic reconstruction technique (SART) for the reconstruction from the projection data. The inventors can extend the 2D SART reconstruction described by Andersen and Kak to 3D.

The inventors have chosen to use SART for several reasons: 1) it removes the salt and pepper noise typically associated with algebraic reconstruction technique (ART) methods with out the need for a relaxation term, 2) it is computationally more efficient than ART and simultaneous iterative reconstruction technique (SIRT), typically requiring only one iteration, 3) it has proven to be superior to ART and SIRT for dealing with non-uniform ray density associate with bent rays, 4) requires fewer equations than ART and SIRT, since it does not require over constraint of the system (we can create a finer grid (more voxels) with the same number of projections), and 5) it is more robust than filtered back-projection reconstruction, although more computationally costly.

The inventors need to form an image of the local speed-of-sound, or equivalently the refractive index, from measurements of transit-time and the known distance between transceiver elements. The inventors can relate the transit-time to an integral of the refractive index over the ray connecting the transmitter to the receiver. The inventors can write:

$$\int_a^b (1 - n(x, y, z)) ds = -V_w(T - T_w)$$

where $n=V_w/V(x,y,z)$, [V is velocity] the ratio of the speed-of-sound in water to the speed-of-sound in tissue, $T_w$ is the transit-time in water and T is the transit-time in tissue.

9. Calculate Bent Rays

The inventors can extend the 2D ray-tracing approach of Andersen to 3D. The inventors can use a spherical geometry with the origin in the center of the 3D image volume. Planes passing through the center can be rotated around both the X- and Y-axis with rays being project from both sides of the planes in a fashion similar to the 2D method of Andersen. This geometry ensures coverage of the 3D volume by this new geometry. A trilinear interpolation can be used in the required rebinning process. An alternative approach, called fast marching methods, is potentially more accurate and equivalent computationally. Using the eikonal formulation, we solve this differential equation using fast marching methods. A surface propagates through the volume, moving with speed based on the current refractive index estimate. Ray paths can be estimated by tracing perpendicular to the evolving front.

10. Iterate?

Have the convergence criteria been met?

11. 3D SART for Slope of Insertion Loss vs. Frequency

Once a final speed-of sound image is determined the final ray paths can be used in the reconstructions of insertion loss.

The inventors can reconstruct an image of insertion loss vs. frequency using SART. The integral of insertion loss can be measured between each transmitter-receiver pair. The inventors can reconstruct the spatial distribution of insertion loss, as well as, compute the slope and intercept with respect to frequency at each location in the image. The addition of sound-attenuation measurements to speed measurements has been shown to add to the discriminatory power of UCT for breast cancer. However, the errors in attenuation measurements due to refraction and reflection of sound can be quite large. It has also been shown that the slope of attenuation vs. frequency is useful for differentiating malignant from non-malignant tissue. Therefore, the inventors can measure attenuation at multiple frequencies along the same paths. Since reflection and refraction are frequency independent, the signal from all frequencies can have traversed the same path, and as such can minimize the effects of reflection and refraction. The inventors can then reconstruct an image, which is essentially the slope of attenuation vs. frequency. Note the intercept of attenuation vs. slope can also be reconstructed, as well as, attenuation itself for each individual frequency. In reality, the inventors cannot measure attenuation but insertion loss.

12. Display

In order to fully examine the UCT image of the breast in detail, it can be necessary to scan through the breast slice by slice. It has been shown that the performance of radiologists improves with 3D display systems. Rendering techniques such as sum projection, maximum intensity projection and gradient-based volume rendering can help focus attention on suspicious regions. The user interface can enable switching between volume and slice views. Multimodal displays using linked cursors and color overlays of speed-of-sound and ultimately attenuation, in addition to computed features such as texture, can facilitate the visual integration of various image parameters. The planned display software can run on a standard PC.

One embodiment of the system of the present invention includes one or more of the following features and functions:

1. Temperature controlled water bath
   a. Heated
   b. Insulated
2. Anechoic chamber
3. Patient interface
   a. Table
   b. Positioning
4. Drain, fill and/or filtering of water bath
5. Controller
   a. Timing
   b. Sequencing
6. Transmit and Receive circuitry
   a. Pulse
   b. Shaped signal
   c. Amplification
7. Transducers
   a. Small
   b. Piezoelectric
   c. Omni, or at least hemispherical, emission
   d. Multiple Frequencies via
      i. Single resonant
      ii. Multiple resonant
      iii. Off resonant
8. Cylindrical arrangement of transducers
9. Analog to digital conversion
10. Digital Signal Processing
    a. Filtering
    b. Transmit time
       i. Threshold
       ii. Cross correlation
    c. Insertion loss
       i. Amplitude difference
       ii. Integral difference
11. Reconstruction
    a. Algebraic methods assuming straight rays for refractive index
    b. Create new projections
       i. Method of Anderson extended to 3D
       ii. Marching sets
    c. Iterate reconstruction
    d. Reconstruct slope of insertion loss vs. frequency using rays determined from refractive index image
12. Image display
    a. Orthogonal views
    b. Rendered views
    c. Linked windows
    d. Fused images
13. 3D acquisition, 3D reconstruction, 3D displays
14. Digital image format
15. Potential for computer assisted diagnosis There are several potential uses for the present invention UCT imaging system. The first is as an adjunctive diagnostic exam. After a lesion has been detected either by mammography or palpation, the imaging system of the present invention could be used to quantitatively classify tissue. Non-invasive tissue classification is the preferred for quantitative classification of tissue.

The 3D UCT imaging system of the present invention has the ability to characterize and differentiate lesion types, and therefore, 3D UCT may reduce the number of invasive biopsies performed. Tumor size is an important parameter for tumor staging and as a predictor of outcome. The important size categories are: 0.5, 1.0, 2.0, and 5.0 cm. In one embodiment imaging system of the present invention the imaging resolution is 1 mm. The time elapsed for performing a scan is optimally about half as long as for a screening scan (only one breast) unless there is the need for an intervenous injection of a contrast agent with two scans being required.

The 3D UCT imaging system of the present invention enables screening to begin at an early age, such as before age 40, so as to image the dense breast of young woman. The 3D UCT imaging system of the present invention can be useful as an alternative modality when X-ray mammography is not indicated. Also, it may prove useful to have patients alternate between X-ray mammography and 3D UCT imaging of the present invention to improve detection rate. The 3D UCT imaging system of the present invention is safe, quick, and comfortable, making it idyllic for a screening modality. So long as patient positioning can be performed efficiently, screening scans could take no more than 5 to 10 minutes total for both breasts.

The 3D UCT imaging system of the present invention can create a 3D image of the breast. Utilization of image-guided surgery can allow a physician to pinpoint the 3D location of a lesion in order to perform a biopsy or remove the entire mass without the need for additional technologies such as 2D echo ultrasound. The 3D UCT imaging system of the present invention can be used for image guided surgery is in addition to the other uses described herein.

The 3D UCT imaging system of the present invention is designed considering a scan cost factor. Therefore the goal of the present invention is to perform scans using the 3D UCT imaging system while keeping cost in a range similar to that of X-ray mammography.

Figure 4:
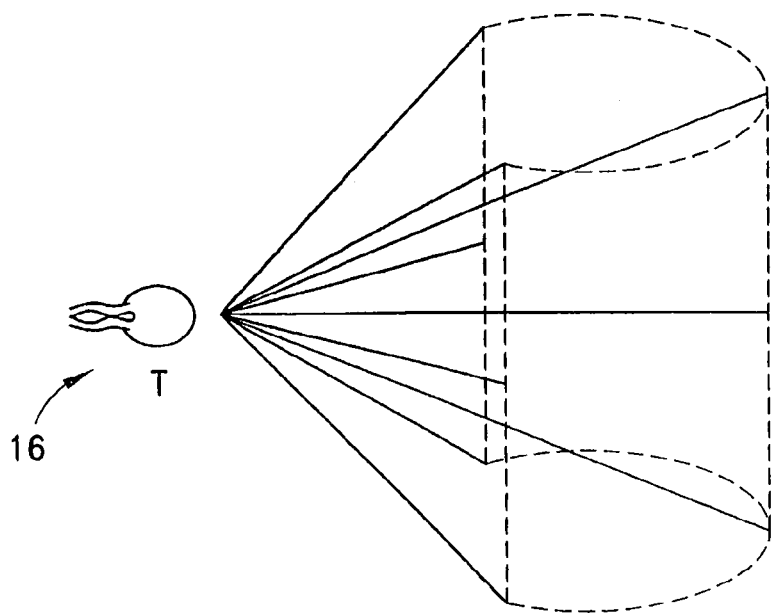
FIG. 4 is an illustration of a cone beam shaped acquisition formed using the system of the present invention.

Empherical Case:

The inventors created a 2D prototype imager in order to make portions of the apparatus of the present invention operational. The description of the empherical case references a 2D configuration but is not intended to limit the novel 3D imaging system of the present invention. (See FIG. 4.) It consists of a ring of 32 elements (2 mm piezoelectric transducers, 1 MHz) using a section of PVC tubing. The crystals are extended from the inner surface of the tubing by 6 mm using plastic offsets, so that the crystals form a ring about 67 mm in diameter. These crystals are excited sequentially and all 31 other crystals "listen". The inventors used a threshold detection method to record the time it took for each crystal to receive the transmitted signal. All 32 crystals were excited in 1/30 of a second. The inventors repeated the measurements at 30 Hz for 5 seconds resulting in 150 measurements for each projection. Also, since each crystal acts as both a transmitter and receiver, each individual projection has been duplicated. Therefore, using 32 crystals, 498 unique projections are acquired. The inventors made two sets of measurements using the finger of a latex glove filled with hand soap (19 mm diameter): 1) one placed in the center; and 2) another placed off center. The inventors reconstructed images using two methods: 1) filtered back projection; and 2) algebraic reconstruction (ART). With both methods, the measurements used were the difference between baseline (water only) transit-times and the phantom transit-times. This measurement gives an integral of 1-n, where n is the index of refraction. The reconstructed images showed the index of refraction to be 1.08 for the hand soap object.

In the case of filtered back projection, the inventors first sorted the measurements, each corresponding to a ray across the ring, into parallel rays. In this way, there are 64 projection angles, each unevenly sampled with 16 samples. Each projection was re-sampled to 53 samples and filtered with a windowed absolute value filter. The image was reconstructed to a 53×53 matrix (1.3×1.3 mm).

For ART, a linear algebraic solution is determined. Here, WP=Q, where P is the image vector, Q is the projection (measurement) vector, and W is the weight matrix. W is determined by computing the length of the ray segment crossing each pixel for each ray. The reconstructed image was 20×20 pixels (3.4×3.4 mm). Pixels outside of the ring were constrained to be zero. The system was over constrained and a least-squares solution (pseudo-inverse) for P was determined. The resulting image was smoothed.

The finger appears larger than its actual size in the images likely in part due to refraction. Early investigators notes that areas of higher speeds appear larger due to refraction using straight-ray assumptions. A 3D ray-tracing algorithm can be implemented into reconstructions, the goal of which is to minimize refraction error.

To show how increasing the number of piezoelectric elements can affect the image, the inventors mathematically "rotated" the 32 elements of the 2D prototype 16 times (similar to using 128 elements) for the centered phantom (this can be done because of symmetry). Using filtered back projection, with the other reconstruction parameters the same, reconstruction artifacts are greatly reduced In an attempt to test the resolution of the 2D prototype, the inventors imaged a drinking straw (6 mm diameter) filled with shampoo. Insertion loss was then reconstructed for the drinking straw/shampoo phantom. A Textronics, Model 220 digital oscilloscope was used to capture the received signal for each combination of elements. This acquisition took approximately thirty minutes for one complete data set (only 4 repeat measurements as compared to 150 for the previous examples). The time limiting factor is the use of a serial interface between the digital oscilliscope (A to D Converter) and the PC for data transfer. In a 3D prototype, a GPIB General Purpose Interface Businterface can be used to increase the transfer rate by a factor of more than 60 times. This acquisition would have been less than 30 seconds. using a GPIB interface. The maximum amplitude of the first received pulse was determined for each element pair with and without the straw in the imager. An image, using the difference between these values (insertion loss), was then reconstructed using filtered back projection. Although the image is noisy, the straw appears in the center of the image, and its diameter was estimated to be between 7.5 and 8.5 mm.

Signal Detection

It is crucial that transit-time measurements be done precisely so that the ultimate, quantitative, reconstructed image accurately reflects the true tissue properties. The simplest method for detection of the ultrasonic pulse at the receiving transducer is based on a single threshold. This "leading edge" technique detects a pulse when the signal exceeds a threshold that is set above the noise level. Since the earliest part of the pulse is likely to follow the straightest path, detection based on the leading edge can minimize the effects of refraction. This approach is straightforward to implement and can be used as an initial basis for comparison. However, low amplitude signals from high speed-of-sound regions can distort the measurement if they exceed the threshold.

A more effective method of pulse detection may be to use cross-correlation. Here, the pulse waveform is acquired and compared to a reference pulse that was acquired in water. The transit-time is determined by matching the acquired signal to the reference signal. The offset that best matches according to a cross-correlation gives the transit-time. No threshold needs to be set, and therefore, small amplitude signals cannot confound the detection. In practice, further refinements may be necessary including repeat measurements and spatial averaging of transit-times. Note however, that simple thresholding may be superior in cases of high attenuation.

The addition of sound-attenuation measurements to speed measurements has been shown to add to the discriminatory power of UCT for breast cancer. However, the errors in attenuation measurements due to refraction and reflection of sound can be quite large. It has also been shown that the slope of attenuation vs. frequency is useful for differentiating malignant from non-malignant tissue. Therefore, we can measure attenuation at multiple frequencies (6 MHz and 8 MHz) along the same paths. Since reflection and refraction are frequency independent, the signal from both frequencies can have traversed the same path, and as such can minimize the effects of reflection and refraction. We can then reconstruct an image, which is essentially the slope of attenuation vs. frequency. Note the intercept of attenuation vs. slope can also be reconstructed. In reality, we cannot measure attenuation but insertion loss. Insertion loss is defined as the difference in received energy between a water-only maximum received signal and the maximum received signal after an object has been placed in the chamber. Insertion loss is really the sum of all energy loss from true attenuation, diffraction, refraction and reflection.

At each element we can digitize the received signal using the high-speed acquisition capabilities of a conventional oscilloscope (Tektronix TDS-220) at the rate of 1 gigasamples per second over a 10 μsec window centered around the leading edge of the received ultrasound pulse. If the transfer rate to the PC is too slow the inventors can utilize a PC-based A to D board to decrease the acquisition time. The signal can then be analyzed offline (in the future we plan to perform these calculations online, using Digital Signal Processing (DSP) technologies) for the determination of the arrival time (using the threshold technique) and the insertion loss. Both of these parameters can then be reconstructed.

Reconstruction

The inventors need to form an image of the local speed-of-sound, or equivalently the refractive index, from measurements of transit-time and the known distance between transceiver elements. The inventors can relate the transit-time to an integral of the refractive index over the ray connecting the transmitter to the receiver. The inventors can write:

$$\int_a^b (1 - n(x, y, z)) ds = -V_w(T - T_w)$$

where $n = V_w/V(x,y,z)$, [V is velocity] the ratio of the speed-of-sound in water to the speed-of-sound in tissue, $T_w$ is the transit-time in water and T is the transit-time in tissue.

The inventors can develop a 3D simultaneous algebraic reconstruction technique (SART) for the reconstruction from the projection data. The inventors can extend the 2D SART reconstruction described by Andersen and Kak to 3D. The inventors can also reconstruct an image of insertion loss vs. frequency using SART. The integral of insertion loss can be measured between each transmitter-receiver pair. The inventors can reconstruct the spatial distribution of insertion loss, as well as, compute the slope and intercept with respect to frequency at each location in the image.

The inventors have chosen to use SART for several reasons: 1) it removes the salt and pepper noise typically associated with algebraic reconstruction technique (ART) methods with out the need for a relaxation term, 2) it is computationally more efficient than ART and simultaneous iterative reconstruction technique (SIRT), typically requiring only one iteration, 3) it has proven to be superior to ART and SIRT for dealing with non-uniform ray density associate with bent rays, 4) requires fewer equations than ART and SIRT, since it does not require over constraint of the system (we can create a finer grid (more voxels) with the same number of projections), and 5) it is more robust than filtered back-projection reconstruction, although more computationally costly.

The inventors can extend the 2D ray-tracing approach (See Section B1) of Andersen to 3D. We can use a spherical geometry with the origin in the center of the 3D image volume. Planes passing through the center can be rotated around both the X- and Y-axis with rays being project from both sides of the planes in a fashion similar to the 2D method of Andersen. This geometry ensures coverage of the 3D volume by this new geometry. A trilinear interpolation can be used in the required rebinning process. An initial image of the speed-of-sound can be reconstructed assuming straight rays, then the ray tracing procedure can be employed iteratively to reach the final image. Once a final speed-of sound image is determined the final ray paths can be used in the reconstructions of insertion loss.

For each reconstructed parameter, the image can be 128×128 pixels with an in-plane field of view of 128×128 mm, resulting in pixel dimensions of 1 mm×1 mm. The 'z' dimension of each voxel can be 4 mm, equal to the space between each ring of piezoelectric elements. The 'z' resolution can be improved by incorporating axial translation into the chamber design. Pixel/voxel number and size is also variable. Isotropic voxels (same dimension in all three directions) is also a feature of our design. Many image modalities have good in plane resolution but have thick slices. This creates something called partial volume error. Partial volume error is blurring of the true tissue properties due to averaging of large sections of the tissue into one value that is displayed in the image.

Display

In order to fully examine the UCT image of the breast in detail, it can be necessary to scan through the breast slice by slice. It has been shown that the performance of radiologists improves with 3D display systems. Rendering techniques such as sum projection, maximum intensity projection and gradient-based volume rendering can help focus attention on suspicious regions. The user interface can enable switching between volume and slice views. Multimodal displays using linked cursors and color overlays of speed-of-sound and ultimately attenuation, in addition to computed features such as texture, can facilitate the visual integration of various image parameters. The planned display software can run on a standard PC.

Small Animal

In an alternate embodiment of the invention, the object to be imaged is a small animal, i.e. rat or mouse. The non-invasive, structural, in vivo imaging of small animals has many utilities. To image a small animal, higher frequency (12 MHz to 15 MHz) piezoelectric elements than those used for imaging of a breast are used. The higher frequency is to further limit diffraction of the ultrasound and thus achieve the higher resolution required for imaging of small animals. Higher frequencies are usable in the imaging of small animals because of the amount of attenuation of ultrasound by the body of a small animal is much less than that of a human breast. The image chamber for a small animal would be smaller than the chamber for a human breast. For example the diameter could be 60 mm with a height of 100 mm.

A small harness is required to suspend the body of the animal into the image chamber. The animal is suspended tail down and is held stationary for imaging. Physiologic monitoring of the animal is possible without hindering the system's ability to image the animal. To reduce image artifacts due motion of the animal, investigators may wish to paralyze the animal. Paralysis necessitates mechanical respiration. A means for mechanical respiration can thus be part of the system.

In the United States there can be an estimated 40,000 deaths in 2001 due to breast cancer. However, early detection and diagnosis improves the chance of survival. X-ray mammography misses 8–22% of palpable cancers, uses ionizing radiation, and is unable to distinguish lesion types. In the best facilities, only 60% of cancers are detected when they are smaller than 1 cm. Approximately 75% of the approximately 800,000 costly breast biopsies per year (an average of $3,500 each) are benign. Therefore, there is a need for a non-invasive, safe, sensitive and specific modality to diagnosis and/or screen for breast cancer. 3D UCT may provide such a modality. The UCT imager has promise to perform the following three tasks:

The final limitation is that like any new technology, there can be resistance from the status quo amongst radiologists. The advantages of the technique can have to be shown to be worth the effort to learn and/or replace existing modalities. The inventors feel that the potential advantages of a 3D UCT imager, including no ionizing radiation, no need for compression (with the additional benefit of no distortion of 3D localization of any lesion detected), fast imaging time, and the potential for tissue classification can overcome this resistance.

An advantage of the embodiments of the present invention is that it can provide imaging more quickly than prior methods and without cumulative effects of radiation. Other advantages of the invention will in part be obvious and will in part be apparent from the specification. The aforementioned advantages are illustrative of the advantages of the present invention.

The invention claimed is:

1. An apparatus for forming a three-dimensional ultrasound computed tomography image of a target comprising:
    an imaging chamber having a plurality of cylindrical rings, said plurality of cylindrical rings having a plurality of transceivers disposed thereon;
    a controller coupled to each of said transceivers for selectively activating one of said transceivers to transmit a wave at said target and several of said transceivers to receive the waves propagated through said target; and
    an imaging processing unit coupled to said plurality of transceivers for processing information from said imaging chamber and for constructing a three-dimensional image of said target therefrom.

2. The apparatus as set forth in claim 1, wherein the apparatus further comprises a display unit coupled to said image processing unit for visualizing said three-dimensional image of said target.

3. The apparatus as set forth in claim 1, wherein said transceivers are omni-directional transceivers.

4. The apparatus as set forth in claim 1, wherein said transceivers are comprised of piezoelectric elements.

5. The apparatus as set forth in claim 1, wherein said transceivers include an acoustic coating.

6. The apparatus as set forth in claim 1, wherein said transceivers are hemispherical transceivers.

7. The apparatus as set forth in claim 1, wherein each transceiver generates multiple frequencies.

8. The apparatus as set forth in claim 1, wherein said transceivers are arranged in a alternating frequency pattern wherein each transceiver generates a single frequency.

9. The apparatus as set forth in claim 1, further comprising:
    a fluid disposed in said imaging chamber; and
    a heating/cooling unit with feedback control for heating or cooling said fluid to form an isothermic environment within said imaging chamber.

10. The apparatus as set forth in claim 1, further comprising means for rotating said imaging chamber to a plurality of positions about a central axis such that additional projections of said target are formed from said plurality of positions.

11. A method of imaging a target three-dimensionally comprising the steps of:
    placing a target into an imaging chamber of an ultrasound computed tomography imaging apparatus;
    applying an input waveform to a series of transmitting elements in sequence, said input waveform creating a wave front wherein said wave front propagates through said target;
    receiving said wave front by receiving elements, wherein said receiving elements generate an electrical signal;
    processing said electrical signal; and
    producing an image of said target.

12. The method as set forth in claim 11, further comprising a rotating step after said processing step, wherein said rotating step is followed by said applying, receiving and processing steps, and further wherein said rotating step is repeated a plurality of times.

13. The method as set forth in claim 11, wherein the input waveform is an impulse signal.

14. The method as set forth in claim 11, wherein said processing of said electrical signal includes determining insertion loss.

15. The method as set forth in claim 11, wherein said processing of said electrical signal includes determining transit-time.

16. The method as set forth in claim 11, wherein said target is a human breast.

17. The method as set forth in claim 11, wherein said image is produced using a simultaneous algebraic reconstruction technique (SART) method applied to said processed electrical signals.

18. The method as set forth in claim 17, wherein the SART method is applied iteratively to reconstruct a speed-of-sound image, wherein bent rays due to three dimensional (3D) refraction are estimated at each iteration.

19. The method as set forth in claim 18, wherein said bent rays due to 3D refraction are computed by ray tracing with rebinning in three dimensions.

20. The method as set forth in claim 18, wherein said bent rays due to 3D refraction are computed by fast marching methods.

21. The method as set forth in claim 18, wherein the SART method is used to reconstruct an image of insertion loss, wherein the image of insertion loss is reconstructed using estimated bent rays after final iteration.

22. The method as set forth in claim 18, wherein the SART method is used to reconstruct an image of insertion loss versus frequency, wherein the image of insertion loss versus frequency is reconstructed using estimated bent rays after final iteration.

23. A method of imaging a target to produce a three-dimensional image comprising the steps of:
    selecting a plurality of transceivers to act as transmitting elements;
    selecting a plurality of transceivers to act as receiving elements;
    placing said target to be imaged into an imaging chamber;
    applying an input waveform to said transmitting elements;
    creating a wave front that propagates through said imaging chamber and said target, wherein said wave front excites said receiving elements;
    producing an electrical signal by said receiving elements;
    amplifying said electrical signal;
    digitizing said electrical signal;
    processing said electrical signal;
    reconstructing data received by said receiving elements; and
    displaying said reconstructed data on a display unit.

* * * * *